US009523656B2

(12) United States Patent
Tan et al.

(10) Patent No.: US 9,523,656 B2
(45) Date of Patent: Dec. 20, 2016

(54) RUGGEDIZED APPARATUS FOR ANALYSIS OF NUCLEIC ACID AND PROTEINS

(71) Applicant: NETBIO, INC., Waltham, MA (US)

(72) Inventors: Eugene Tan, Lexington, MA (US); Heung Chuan Lam, Newton, MA (US); Gregory John Kellogg, Cambridge, MA (US)

(73) Assignee: NetBio, Inc., Waltham, MA (US)

( * ) Notice: Subject to any disclaimer, the term of this patent is extended or adjusted under 35 U.S.C. 154(b) by 0 days.

(21) Appl. No.: 13/834,226

(22) Filed: Mar. 15, 2013

(65) Prior Publication Data

US 2013/0199933 A1 Aug. 8, 2013

Related U.S. Application Data

(63) Continuation of application No. 13/482,765, filed on May 29, 2012, which is a continuation of application No. 11/132,712, filed on May 19, 2005, now Pat. No. 8,206,974.

(51) Int. Cl.
*G01N 27/447* (2006.01)
(52) U.S. Cl.
CPC .. *G01N 27/44791* (2013.01); *G01N 27/44721* (2013.01)
(58) Field of Classification Search
None
See application file for complete search history.

(56) References Cited

U.S. PATENT DOCUMENTS

| 2,817,264 | A | | 12/1957 | Pearson |
| 4,170,616 | A | | 10/1979 | Jebens |
| 4,811,218 | A | | 3/1989 | Hunkapiller et al. |
| 5,126,022 | A | | 6/1992 | Soane et al. |
| 5,126,629 | A | | 6/1992 | Chopy |
| 5,164,055 | A | | 11/1992 | Dubrow |
| 5,171,534 | A | | 12/1992 | Smith et al. |
| 5,275,710 | A | | 1/1994 | Gombocz et al. |
| 5,290,418 | A | | 3/1994 | Menchen et al. |
| 5,395,502 | A | * | 3/1995 | Pawliszyn ............ 204/603 |
| 5,468,365 | A | | 11/1995 | Menchen et al. |
| 5,545,901 | A | * | 8/1996 | Pentoney et al. ...... 250/458.1 |

(Continued)

FOREIGN PATENT DOCUMENTS

| WO | WO 00/22424 | 4/2000 |
| WO | WO 02/056004 | 7/2002 |

(Continued)

OTHER PUBLICATIONS

Albarghouthi et al., "Polymeric Matrices for DNA Sequencing by Capillary Electrophoresis," Electrophoresis 2000, vol. 21, pp. 4096-4111.

(Continued)

*Primary Examiner* — Robert T Crow
(74) *Attorney, Agent, or Firm* — Proskauer Rose LLP

(57) ABSTRACT

The invention provides methods and systems for ruggedizing a nucleic acid analyzing apparatus. The ruggedized apparatus can be used reliably and effectively in uncontrolled environments, such as, for example at a crime scene to collect and analyze forensic data, as well as in semi-controlled environments, such as, for example at a point of care location.

7 Claims, 32 Drawing Sheets

(56) References Cited

U.S. PATENT DOCUMENTS

| | | | |
|---|---|---|---|
| 5,614,726 | A | 3/1997 | Kaye et al. |
| 5,750,015 | A | 5/1998 | Soane et al. |
| 5,770,029 | A | 6/1998 | Nelson et al. |
| 5,779,868 | A | 7/1998 | Parce et al. |
| 5,821,058 | A | 10/1998 | Smith et al. |
| 5,858,187 | A | 1/1999 | Ramsey et al. |
| 5,858,188 | A | 1/1999 | Soane et al. |
| 5,858,195 | A | 1/1999 | Ramsey |
| 6,120,667 | A | 9/2000 | Hayashizaki et al. |
| 6,131,072 | A | 10/2000 | Holden et al. |
| 6,143,152 | A | 11/2000 | Simpson et al. |
| 6,153,073 | A | 11/2000 | Dubrow et al. |
| 6,207,031 | B1 | 3/2001 | Adourian et al. |
| 6,225,635 | B1 | 5/2001 | Brewer et al. |
| 6,235,175 | B1 | 5/2001 | Dubrow et al. |
| 6,251,247 | B1 | 6/2001 | Mitsuhashi et al. |
| 6,280,589 | B1 | 8/2001 | Manz et al. |
| 6,292,499 | B1 | 9/2001 | Pearson et al. |
| RE37,606 | E | 3/2002 | Guttman |
| 6,486,963 | B1 * | 11/2002 | Holec ............ 356/601 |
| RE37,941 | E | 12/2002 | Guttman |
| 6,498,497 | B1 | 12/2002 | Chow et al. |
| 6,515,753 | B2 | 2/2003 | Maher et al. |
| 6,563,584 | B1 | 5/2003 | Yurino et al. |
| 6,598,545 | B2 | 7/2003 | Ryaboy et al. |
| 6,606,273 | B1 | 8/2003 | Guo et al. |
| 6,733,645 | B1 | 5/2004 | Chow |
| 6,733,648 | B2 | 5/2004 | Okano et al. |
| 6,875,619 | B2 | 4/2005 | Blackburn |
| 6,893,879 | B2 | 5/2005 | Petersen et al. |
| 6,960,286 | B2 | 11/2005 | Manz et al. |
| 8,173,417 | B2 * | 5/2012 | Tan et al. ............ 435/287.2 |
| 8,206,974 | B2 * | 6/2012 | Tan et al. ............ 435/287.2 |
| 2002/0015147 | A1 | 2/2002 | Maher et al. |
| 2002/0042125 | A1 | 4/2002 | Petersen et al. |
| 2002/0096432 | A1 | 7/2002 | Yamakawa et al. |
| 2003/0021016 | A1 | 1/2003 | Grier |
| 2003/0118477 | A1 | 6/2003 | Liljestrand et al. |
| 2003/0152927 | A1 | 8/2003 | Jakobsen et al. |
| 2003/0190608 | A1 | 10/2003 | Blackburn |
| 2004/0011975 | A1 * | 1/2004 | Nicoli et al. ............ 250/574 |
| 2004/0071597 | A1 | 4/2004 | Hattori et al. |

FOREIGN PATENT DOCUMENTS

| | | |
|---|---|---|
| WO | WO 02/063288 | 8/2002 |
| WO | WO 20005/029062 | 3/2005 |

OTHER PUBLICATIONS

Bosserhoff et al., "Use of Capillary Electrophoresis for High Throughput Screening in Biomedical Applications, a Minireview," Combinational Chemistry & High Throughput Screening, 2000, issue 3, pp. 455-466.

Budowle et al., "CODIS and PCR Based Short Tandem Repeat Loci: Law Enforcement Tools," Second European Symposium on Human Identification, 1998, pp. 73-88.

Ewing et al., "Base-Calling of Automated Sequencer Traces Using Phred I. Accuracy Assessment," Genome Research, 1998, vol. 8, pp. 175-185.

Ewing et al., "Base-Calling of Automated Sequencer Traces Using Phred II. Error Probabilities," Genome Research, 1998, vol. 8, pp. 186-194.

Ferrance et al, "Exploiting Sensitive Laser-Induced Fluorescence Detection on Electrophoretic Microchips for Executing Rapid Clinical Diagnostics," Luminescence, 2001, issue 16, pp. 79-88.

Goedecke et al., "A High-Performance Multilane Microdevice System Designed for the DNA Forensics Laboratory," Electrophoresis 2004, vol. 25, pp. 1678-1686.

Li et al., "An Estimate of the Crosstalk Matrix in Four-Dye Fluorescence-Based DNA Sequencing," Electrophoresis 1999, vol. 20, issue 1, pp. 1433-1442.

Mitnik et al., "High-Speed Analysis of Multiplexed Short Tandem Repeats with an Electrophoretic Microdevice," Electropheresis 2002, vol. 23, pp. 719-726.

Ruiz-Martinez et al., "DNA Sequencing by Capillary Electrophoresis with Replaceable Linear Polyacrylamide and Laser-Induced Fluorescence Detection," Anal. Chem., vol. 65, 1993, pp. 2851-2858.

Tong et al., *Semiconductor Wafer Bonding: Science and Technology*, Wiley Publishers, Nov. 1998, Chapters 4, 5, and 10.

Woolley et al., "High-Speed DNA Genotyping Using Microfabricated Capillary Array Electrophoresis Chips," Analytical Chemistry, vol. 69, No. 11, Jun. 1, 1997, pp. 2181-2186.

Woolley et al., "Ultra-High-Speed DNA Sequencing Using Capillary Electrophoresis Chips," Analytical Chemistry, vol. 67, No. 20, Oct. 15, 1995, pp. 3676-3680.

Stanford Research Systems; www.thinksrs.com/products/PS300htm; copyright 2003.

\* cited by examiner

Sequence of the Amplicon B.FR.HXB2

```
         0---------1---------2---------3---------4---------5---------6
         123456789012345678901234567890123456789012345678901234567890
   1  CTAGAGGGAATTTCTTCAGAGCAGACCAGAGCCAACAGCCCCACCAGAAGAGAGCTTCA
  61  GGTCTGGGGGTAGAGACAACAACTCCCCCTCAGAAGCAGGAGCCGATAGACAAGGAACTGT
 121  ATCCTTTAACTTCCCTCAGATCACTCTTTGCAACGACCCCTCGTCACAATAAAGATAGG
 181  GGGGCAACTAAAGGAAGCTCTATTAGATACAGGAGCAGATGATACAGTATTAGAAGAAAT
 241  GAGTTTGCCAGGAAGATGGAAACCAAAAATGATAGGGGGAATTGGAGGTTTTATCAAAGT
 301  AAGACAGTATGATCAGATACTCATAGAAATCTGTGGACATAAAGCTATAGGTACAGTATT
 361  AGTAGGACCTACACCTGTCAACATAATTGGAAGAAATCTGTTGACTCAGATTGGTTGCAC
 421  TTTAAATTTTCCCATTAGCCCTATTGAGACTGTACCAGTAAAATTAAAGCCAGGAATGGA
 481  TGGCCCAAAAGTTAAACAATGGCCATTGACAGAAGAAAAAATAAAAGCATTAGTAGAAAT
 541  TTGTACAGAAATGGAAAAGGAAGGGAAAATTTCAAAATTGGGCCTGAGAATCCATACAA
 601  TACTCCAGTATTTGCCATAAAGAAAAAAGACAGTACTAAATGGAGAAAATTAGTAGATTT
 661  CAGAGAACTTAATAAGAGAACTCAAGACTTCTGGGAAGTTCAATTAGGAATACCACATCC
 721  CGCAGGGTTAAAAAAGAAAAAATCAGTAACAGTACTGGATGTGGGTGATGCATATTTTTC
 781  AGTTCCCTTAGATGAAGACTTCAGGAAGTATACTGCATTTACCATACCTAGTATAAACAA
 841  TGAGACACCAGGGATTAGATATCAGTACAATGTGCTTCCACAGGGATGGAAAGGATCACC
 901  AGCAATATTCCAAAGTAGCATGACAAAAATCTTAGAGCCTTTTAAAAAACAAAATCCAGA
 961  CATAGTTATCTATCAATACATGGATGATTTGTATGTAGGATCTGACTTAGAAATAGGGCA
```

FIG. 20A-1

```
1021  GCATAGAACAAAAATAGAGGAGCTGAGACAACATCTGTTGAGGTGGGACTTACCACACC
1081  AGACAAAAACATCAGAAAAGAAGAACCTCCATTCCTTTGGATGGGTTATGAACTCCATCCTGA
1141  TAAATGGACAGTACAGCCTATAGTGCTGCCAGAAAAAGACAGCTGGACTGTCAATGACAT
1201  ACAGAAGTTAGTGGGAAATTGAATTGGGCAAGTCAGATTTACCCAGGATTAAAGTAAG
1261  GCAATTATGTAAACTCCTTAGAGGAACCAAAGCACTAACAGAAGTAATACCACTAACAGA
1321  AGAAGCAGAGCTAGAACTGGCAGAAAACAGAGATTCTAAAAGAAGCAGTACATGGAGT
1381  GTATTATGACCCATCAAAAGACTTAATAGCAGAAATACAGAAGCAGGGGCAAGGCCAATG
1441  GACATATCAAATTTATCAAGAGCCATTTAAAAATCTGAAAACAGGAAAATATGCAAGAAT
1501  GAGGGGTGCCCACACTAATGATGTAAAAGACTCCTAAATTTAAACTACCCATACAAAAGGAAAC
1561  AGAAAGCATAGTAATATGGGGAAAGACTCCTAAATTTAAACTACCCATACAAAGGAAAC
1621  ATGGGAAACATGGTGGACAGAGTATTGGCAAGCCACCTGGATTCCTGAGTGGGAGTTTGT
1681  TAATACCCCTCG 123456789012345678901234567890123456789012345678901234567890
      0--------1---------2---------3---------4---------5---------6
```

FIG. 20A-2

Unedited sequence

```
    0---------1---------2---------3---------4---------5---------6
    1234567890123456789012345678901234567890123456789012345678901234567890
  1 TAGCCCTATTGAGACTGTACCAGTAAAATTAAAGCCAGGAATGGATGGCCCAAAAGTTAA
 61 ACAATGGCCATTGACAGAAGAAAAATAAAAAGCATTAGTAGAAATTTGTACAGAAATGGA
121 AAAGGAAGGGAAATTTCAAAAATTGGGCCTGAGAATCCATACAATACTCCAGTATTGC
181 CATAAAGAAAAAAGACAGTACTAAATGGAGAAAATTAGTAGATTTCAGAGAACTTAATAA
241 GAGAACTCAAGACTTCTGGGAAGTTCAATTAGGAATACCACATCCCGCAGGGTTAAAAAA
301 GAAAAAATCAGTAACAGTACTGGATGTGGGTGATGCATATTTTTCAGTTCCCTTAGATGA
361 AGACTTCAGGAAGTATAC

Manually inspected and corrected sequence

```
         0         1         2         3         4         5         6
         1234567890123456789012345678901234567890123456789012345678901234567890
   1 AAGTAAGACAGTATGATCAGATACTCATAGAAATCTGTGGACATAAAGCTATAGGTACAG
  61 TATTAGTAGGACCTACACCTGTCAACATAATTGGAAGAAATCTGTTGACTCAGATTGGTT
 121 GCACTTTAAATTTCCCATTAGCCCTATTGAGACTGTACCAGTAAAATAAAGCCAGGAA
 181 TGGATGGCCCAAAGTTAAACAATGGCCATTGACAGAAGAAAATTCAAAAATAAAGCATTAGTAG
 241 AAATTTGTACAGAAATGGAAAAGGAAGGGAAAAAAAGACAGTAAAATTGGGCCTGAGAATCCAT
 301 ACAATACTCCAGTATTTGCCATAAAGAGAACTCAAGACTTCTGGGAAGTTCAATAGGAATACTAG
 361 ATTTCAGAGAACTTAATAAGAGAACTCAAGACTTCTGGGAAGTTCAATAGGAATACCAC
 421 ATCCCGCAGGGTTAAAAAAGAAAAAATCAGTAACAGTACTGGATGTGGGTGATGCATATT
 481 TTTCAGTTCCCTTAGATGAAGACTTCAGGAAGTATACTGCATTTACCATACCTAGTATAA
 541 ACAA 1234567890123456789012345678901234567890123456789012345678901234567890
         0         1         2         3         4         5         6
```

FIG. 20C (1)

RUGGEDIZED APPARATUS FOR ANALYSIS OF NUCLEIC ACID AND PROTEINS

RELATED APPLICATIONS

This application is a continuation of application Ser. No. 13/482,765, filed on May 29, 2012, which is a continuation of application Ser. No. 11/132,712, filed on May 19, 2005, now issued as U.S. Pat. No. 8,206,974. All of these patents and patent applications are owned by the assignee of the instant application and the entire disclosures of each of these patents and patent applications are incorporated herein by reference in their entireties.

FIELD OF THE INVENTION

The invention generally relates to nucleic acid and/or protein analysis devices, and more particularly to ruggedized devices with low power consumption requirements that can be used for nucleic acid and protein sequencing or separation in uncontrolled or semi-controlled environments including mobile labs, physician's offices, hospital labs and other human, veterinary or environmental clinical and/or testing labs and points of care locations.

BACKGROUND

The human genome includes stretches of DNA composed of short tandem repeats (STRs). To date, hundreds of STR loci have been mapped in the human genome. The analysis of such STR loci and STRs is an important tool for genetic linkage studies, forensics, and new clinical diagnostics. For example, forensic case work typically involves separation and analysis of multiple loci. Some tests use the 6 loci test known as the "Second Generation Multiplex" (SGM), together with amelogenin (gender determining marker) and four additional loci, D351358; D19S433; D16S539 and D2S1338. Other commercially available kits simultaneously amplify 15 tetranucleotide STR loci and the amelogenin marker (See, e.g., AmpFlSTR Identifiler PCR Amplification Kit). The United States Federal Bureau of Investigation (FBI), European Network of Forensic Science Institutes (ENFSI) and Interpol generally recognize results from kits including at least the thirteen core STR loci standardized under the Combined DNA Index System (CODIS): CSF1PO, D3S1358; D5S818; D7S820; D8S1179; D13S317; D165539; D18551; D21S11; vWA; FGA; TH01; and TPOX. For a general discussion, see Budowle, B. et al., "CODIS and PCR Based Short Tandem Repeat Loci: Law Enforcement Tools," Second European Symposium on Human Identification, 1998, pages 73-88, hereby incorporated by reference in its entirety.

Studies of the human genome also has revealed, and continues to reveal, the existence of specific mutations or polymorphisms. With increasing frequency, these mutations or polymorphisms are being associated with monogenetic and polygenetic diseases. As a result, the field of molecular diagnostics is growing and expanding. Molecular diagnostic testing uses polymorphic markers, such as, microsatellites and STRs, and the determination of mutations associated with neoplastic and other diseases. For example, the presence of certain viral infections, such as herpes simplex virus (HSV), cytomeglia virus (CMV) and human immunodeficiency virus (HIV) have been diagnosed using amplified and separated DNA fragments. Certain types of cancer diagnosis also is carried out using separation of amplified DNA fragments. Specifically, the diagnosis of B and T cell lymphomas fall into this category. When cancer occurs, a single cell having a single form of rearranged DNA grows at an elevated rate, leading to the predominance of that form of the gene. Separation and identification of the mutated gene can be carried out using conventional or microchip devices. For a discussion of the application of sequencing and separation methods and apparatus to molecular diagnostics, see generally, "Use of Capillary Electrophoresis for High Throughput Screening in Biomedical Applications, A Mini-review," by Bosserhoff et al. in *Combinational Chemistry & High Throughput Screening,* 2000, issue 3, pages 455-66 and "Exploiting Sensitive Laser-Induced Fluorescence Detection on Electrophoretic Microchips for Executing Rapid Clinical Diagnostics," by Ferrance et al. in *Luminescence,* 2001, issue 16, pages 79-88, the disclosures of which are hereby incorporated by reference in their entirety.

A typical STR locus is less than 400 base pairs in length, and includes single repetitive units that are two to seven base pairs in length. STRs can define alleles which are highly polymorphic due to large variations between individuals in the number of repeats. For example, four loci in the human genome CSF1PO, TPOX, THO1, and vWA (abbreviated CTTv) are characterized by an STR allele that differs in the number of repeats. Two repeating units are found at these loci: AATG for TPDX and THO1, and AGAT for CSF1PO and vWA.

In general, STR analysis involves generating an STR profile from a DNA sample, and comparing the generated STR profile with other STR profiles. Generating an STR profile typically involves amplifying an STR locus using PCR or another amplification method, dying or tagging STRs within a DNA sample, separating the tagged STRs within the sample using electrophoresis (applying an electric field), and recording the tagged STRs using a laser or other fluorescence excitation device and a galvanometer or other device to direct the fluorescence excitation device towards a sample and then to a light detector.

One procedure for generating an STR profile uses an elongated gel plate (or slab gel) that is approximately 35 cm long. In general, this process (hereinafter referred to as "the gel plate process") involves depositing a tagged nucleic acid sample (most often DNA, but as one skilled in the art will appreciate, RNA may also be used for some applications) on an area of the gel plate, separating the STRs within the tagged DNA sample on the gel plate using electrophoresis, and scanning the gel plate with a detector to record the tagged STRs. Typically, the gel plate process requires two to three hours to complete.

Another procedure for generating an STR profile uses a capillary that is 50 to 75 microns in diameter. This process (hereinafter referred to as "the capillary process") generally involves electrokinetically injecting a tagged DNA sample at one end of a capillary, and drawing the sample through the capillary using electrophoresis to separate the STRs. A laser beam is used to excite the tagged STRs within the sample to cause the tagged STRs to fluoresce. The fluorescence emitted by the STRs is detected by scanning a portion of the capillary with a fluorescence excitation device, such as, for example a laser.

Typically, STR separation is faster in the capillary process than in the gel plate process. In general, an increase in electrophoresis current results in an increase in STR separation speed, and a higher electrophoresis current typically can be applied to the capillary than to the gel plate because the capillary more easily dissipates heat (caused by the current) that would otherwise skew the separation results. A typical capillary process requires between 10 minutes and one hour to complete.

However, controlling temperature is a critical factor related to the precision of capillary-based DNA separation devices. It illustrates why prior art devices are not suitable for rugged, uncontrolled or semi-controlled environments or applications. Prior art devices utilize an array of sixteen capillaries that are injected and run simultaneously at the same temperature, so intra-run precision can be expected to be high, and data sized relative to an allelic ladder within the run can be expected to be reliable. However, inter-run precision appears to be dependent upon temperature fluctuations. Whenever the temperature changes from run to run, the unknown fragments may not be able to be sized by an allelic ladder in a different run. Fragments lying outside of the bin may be called "off-ladder" alleles or mistyped by falling into an adjacent bin. As a result, samples analyzed using this type of device may be mischaracterized, thereby significantly decreasing the quality of results obtained.

Another procedure for generating an STR profile uses a microfluidic chip process. Microfluidics technology is a term generally used to describe systems fabricated using semiconductor manufacturing techniques to create structures that can manipulate tiny volumes (microliter, nanoliter, or picoliters) of liquid, replacing macroscale analytical chemistry equipment with devices that could be hundreds or thousands times smaller and more efficient. A microfluidic device (chip) is generally characterized by the presence of channels with at least one dimension less than 1 millimeter. Similarly, a microchannel is a channel with at least one dimension that is less than about 1 millimeter. Microfluidic chips offer at least two major advantages as compared to conventional devices. First, the volume of sample and reagents required within these channels is small, allowing minimal sample sizes (generally a few nanoliters) and reducing reagent costs. Second, a system containing such channels and similarly sized electrical or mechanical devices allows a wide array of complex sample manipulations to be performed within a small volume. Finally, a system containing such small structures can be highly multiplexed to allow for simultaneous processing of multiple samples and therefore high throughput operation.

Chips generally are composed of durable transparent glass. A typical chip consists of one or more channels fabricated within a planar substrate with access points for samples to be introduced into the channel. In one embodiment, a channel can consist of a long arm (sometimes referred to as the "long channel") and short arm (sometimes referred to as the "short channel"). An individual STR separation can be performed at each channel. The short arm intersects the long channel near one end of the long arm and at an angle. In some chips, the short arm includes a jog where it intersects the long channel such that portions of the short channel are parallel but not co-linear. Typically, a chip is formed using photolithography and chemical etching techniques to produce channel structures in fused silica wafers. These etched channel structures are bonded to an unetched fused silica wafer to form a complete channel structure.

An STR separation process that uses a chip generally involves orienting the microchip so that it and the channels within lie horizontally (i.e., perpendicular to the direction of gravity) and depositing a sample of tagged DNA over a hole in the upper surface of the microchip that connects with one end of the short channel of a channel pair. Next, the tagged DNA sample is drawn horizontally through the short channel using electrophoresis such that STRs within the sample are partially separated along the short channel. Then, a portion of the sample at the intersection of the long and short channels is further separated along the long channel using electrophoresis. A laser excites the tagged STR which fluoresces. The fluorescences emitted by the STRs is detected and recorded in a manner similar to that of the gel plate and capillary processes.

Conventional high-speed DNA genotyping using a chip is described in an article entitled "High-Speed DNA Genotyping Using Microfabricated Capillary Array Electrophoresis Chips," Analytical Chemistry, Vol. 69, No. 11, Jun. 1, 1997 on pages 2181 through 2186, the teachings of which are hereby incorporated by reference in their entirety. Ultra-high-speed DNA sequencing using capillary electrophoresis chips is described in an article entitled "Ultra-High-Speed DNA Sequencing Using Capillary Electrophoresis Chips," Analytical Chemistry, Vol. 67, No. 20, Oct. 15, 1995 on pages 3676 through 3680, the teachings of which are hereby incorporated by reference in their entirety.

U.S. Pat. No. 6,207,031 issued to Adourian et al., the teachings of which is hereby incorporated by reference in its entirety, describes an automated separation device useful in allelic profiling assays. The separation device described in U.S. Pat. No. 6,207,031 includes a microfabricated channel device having a channel of sufficient dimensions in cross-section and length to permit a sample to be analyzed rapidly. Specifically, the microfabricated channel is filled with a replaceable polyacrylamide matrix operated under denaturing conditions and a fluorescently labeled STR ladder is used as an internal standard for allele identification. Samples analyzed by the assay method can be prepared by standard procedures and only small volumes of assay are required per analysis. This device is capable of repetitive operation and is suitable for automated high-speed and high-throughput applications.

While the separation devices described in U.S. Pat. No. 6,207,031 are efficient at separating a large number of samples in a relatively short amount of time, the device of U.S. Pat. No. 6,207,031 needs to be located in a laboratory setting under a controlled environment. As a result, in field use, such as, for example, use of the above-described devices at a point of care location, such as a doctor's office or at an emergency disaster site is impractical due to the size, energy requirements, and operational (i.e., minimal vibrational impact on sensitive optical equipment) constraints of these devices. In addition, these devices also have high power consumption that limits the utility of these devices in field use.

Thus, there is an unmet need in the industry to ruggedize sequencing and separation devices so that reliable, timely measurements can be obtained in the field or in a non-controlled environment. Further, there is an industry need to provide a commercially available suitably ruggedized sequencing and/or separation device using microfluidics.

SUMMARY OF THE INVENTION

In general, the present invention relates to miniaturized, fast, highly ruggedized nucleic acid sequencing and separation devices. Such devices have uses in physician's offices, hospital laboratories, and other human, veterinary and environmental clinical and/or testing laboratories and other point of care locations. The device of the present invention is suitable for use by unskilled or semi-skilled operators and in environmental locations that are controlled or semi-controlled. The devices of this invention can be expected to deliver significant performance improvements over prior art machines. The devices of the present invention offer the compelling advantages of dramatically reducing the amount of sample and reagent and enabling unique microscale chemistries not possible with macroscale instrumentation, while being able to operate in uncontrolled, semi-controlled, such as, for example a physician's office, or even hostile environments, such as, for example, mobile forensic crime labs, labs or diagnostic stations in harsh or semi-harsh physical locations or environments.

In addition, the devices described in accordance with the present invention can include a novel system that maintains the temperature of the capillary array or its equivalent in a very precise temperature range (e.g., within ±1 degree C.), thereby minimizing run-to-run variation due to changes in temperature in the external environment. As a result, the number of "off-ladder" alleles generated during separation is reduced and thus, the quality of the results obtained is increased over prior art devices. Furthermore, embodiments of the invention described herein are implemented using low power levels, thereby making machines and devices in accordance with the present invention suitable for portable and/or in field use.

The present invention also relates to the support of light detecting and emitting elements including mirrors, lasers, scanners and the like for a DNA separation/sequencing device. The nucleic acid and protein analysis devices of the present invention incorporate specialized laser optics and sensitive optical scanning devices that reproducibly detect microfluidic lanes for satisfactory performance. Since each of the components of a light emission and detection system (e.g., a laser, mirrors, scanners, filters, light detectors) controls some portion of the laser beam's path, any movement or dislocation of a component may cause a disturbance in data collection. As a result of these disturbances, data flow can be interrupted or corrupted, thereby producing incorrect results. Prior art devices using capillary systems also use laser based light emission and detection systems, and therefore, may be adapted for ruggedization using the inventions described herein. The device of the present invention includes a highly ruggedized laser optic and detector system to reproducibly detect microfluidic lanes that minimizes the amount of noise produced in the detected signal as a result of vibration and/or shock. In addition, in certain embodiments, the invention relates to a device that requires less energy than conventional laboratory sequencing devices for electrophoresis and analysis. As a result, the device of the present invention can be used reliably in the field while obtaining high resolution results. The nucleic acid sequencing and separation devices of the prior art also use specialized laser optics and detection systems in capillary lanes. One skilled in the art could readily adapt the laser optics and detection systems generally used in capillary systems to be ruggedized according to the teachings of this invention.

In general, the term "biomolecular analyte" as used herein refers to both non-synthetic and synthetic nucleic acids (e.g., DNA and RNA) and portions thereof, and biological proteins. Described herein are practical ultra-fast techniques for allelic profiling of such biomolecular analyte in the field. In particular, the techniques involve using a microfluidic electrophoresis device to analyze short tandem repeats (STRs) within a nucleic acid or protein sample, or to otherwise separate DNA molecules to allow determination of a nucleic acid sequence. Moreover, as one skilled in the art will appreciate, the sample may be modified or "tagged" to include something that can be detected by a detection device. Tagging may be accomplished by any applicable method, including without limitation, incorporating a dye, chromofore, fluorophore, calorimetric adduct or radioactive adduct into the sample. An assay method of the present invention has made it possible to rapidly achieve baseline-resolved electrophoretic separations of single-locus STR samples. In one embodiment, analysis of samples (e.g., PCR samples) containing loci defined or characterized by an STR which differs in the number or repeats is performed rapidly using the allelic profiling assay described herein. For example, analyses of PCR samples containing four to five loci can be performed in less than about thirty minutes.

Also described herein is a separation device (or test module) useful in an allelic profiling assay of the present invention. The separation device includes a microchannel device having a channel of sufficient dimensions in cross-section and length to permit a sample to be analyzed rapidly. In one embodiment, the separation device consists of a microchannel having a cross-sectional area of from about 300 to about 16,000 square microns in cross-section and about 100 to 500 mm in length. In certain embodiments the microchannel has a preferred cross-sectional area of about 2,500 square microns and a length of 180 mm. A fluorescently labeled STR ladder is used as an internal standard for allele identification. Samples analyzed by the assay method can be prepared by standard procedures and only small volumes (e.g., 4 microliters or less) are required per analysis.

In addition, the devices of this invention can be used in sequencing. Although a large amount of sequencing of the human and other genomes has been completed, there is still good reason to sequence small parts of genomes, especially in a semi-controlled or uncontrolled environment. For example, over 1,000 different mutations have been found in patients with cystic fibrosis. Each of these mutations occurs in a huge gene that encodes a protein of 1,480 amino acids known as the cystic fibrosis transmembrane conductance regulator (CFTR). The gene encompasses over 6,000 nucleotides spread over 27 exons on chromosome 7. Defects in the protein cause various symptoms of the disease. No single mutation is responsible for all cases of cystic fibrosis. People with the disease inherit two mutant genes, but the specific mutation need not be the same. Therefore, the ability to identify the specific mutation has some predictive value. As a further example, the AIDS virus mutates very quickly and a treating physician has a need to be able to sequence the mutated virus at a point of care location so a patient can be sent home with the appropriate therapy to combat the mutated virus at each stage of the course of the disease. In yet another application, an oncologic surgeon making an intra-operative diagnosis in a cancer patient has a need for the ability to receive sequence information at the point of care location.

In general, in one aspect, the invention features a ruggedized apparatus for analyzing a sample of biomolecular analyte. The ruggedized apparatus includes a holder, an electrophoresis device, a low powered light source (i.e., a light source drawing less than about 10 amps at 240 volts), a light detector, and a plurality of optical devices. The holder of the ruggedized apparatus supports a transparent test module having at least one channel disposed with the transparent test module. The electrophoresis device is connected to the holder and provides energy to the transparent test module. The light source emits a light beam that is capable of exciting the sample of biomolecular analyte. The plurality of optical devices mounted within the apparatus transmit the light beam from the light source to the transparent test module to excite the fluorescently tagged biomolecular analyte sample. These optical devices also collect fluorescence from the biomolecular analyte sample and transmit this fluorescence to the light detector.

In one embodiment of the invention, the ruggedized apparatus further includes a portable power supply including a maximum power consumption of 1.5 kVA or less to provide electrical energy to the ruggedized apparatus. In another embodiment of the invention, the electrophoresis device includes a heater to provide thermal energy to the transparent test module and a plurality of pairs of electrodes to provide electrical energy to the plurality of separate microchannels. In another embodiment, the apparatus includes a heater to provide thermal energy to the transparent test module and a plurality of pairs of electrodes to provide electrical energy to the at least one channel.

The plurality of optical devices can be rigidly mounted to a base plate disposed within the apparatus. The light source of the apparatus can be a low power laser, such as a solid state laser or any other suitable laser. The at least one channel of the transparent test module can be a microchannel or a plurality of channels.

In another aspect, the invention features an apparatus for analyzing a sample of biomolecular analyte. The apparatus includes a holder for supporting a transparent test module having at least one microfluidic channel disposed therein. An electrophoresis device is connected to the holder and provides energy to the transparent test module. A low powered light source emits a light beam that excites fluorescence in the sample of biomolecular analyte. A plurality of optical devices mounted within the apparatus transmit the light beam emitted by the light source to the transparent test module and from the transparent test module to a light detector.

In one embodiment, the plurality of optical devices are rigidly mounted to a base plate disposed within the apparatus. In another embodiment, the electrophoresis device comprises a heater to provide thermal energy to the transparent test module and a pair of electrodes to provide electrical energy to the at least one microfluidic channel. In some embodiments, the transparent test module includes a plurality of microfluidic channels. In certain embodiments, the low powered light source includes a low power laser. In some embodiments, the apparatus further includes a portable energy source to provide energy to the apparatus. The portable energy source can have a maximum power consumption of less than about 1.5 kVA.

In another aspect, the invention features an apparatus for processing a sample of biomolecular analyte. The apparatus includes a holder for supporting a transparent test module having at least one channel disposed therein. An electrophoresis device is connected to the holder and provides energy to the transparent test module. A light source for emitting a light beam excites fluorescence in the sample of biomolecular analyte. A plurality of optical devices are rigidly mounted to a base plate formed from a single piece of material. The optical devices disposed on the base plate transmit the light beam emitted by the light source to the transparent test module and from the transparent test module to a light detector. In one embodiment, the base plate is supported by a frame including a damping device to reduce transmission of vibrations generated below the frame to the base plate. The base plate can include a plurality of securing elements for limiting the rotation movement of the plurality of optical devices on the base plate.

In one embodiment, the holder for supporting the transparent test module can include a first member with a pair of electrodes disposed to electrically connect with openings disposed on a transparent test module. A second member includes an automated locking feature to reduce lateral motion of the transparent test module when the transparent test module is positioned between the first member and the second member.

In one embodiment, the light source of the apparatus is a solid state laser, a low power laser, or any other suitable laser. The light detector of the apparatus can include at least five photomultipliers.

In another aspect, the invention features a transparent test module for analyzing a sample of biomolecular analyte. The transparent test module includes at least one fluid channel disposed within a member formed of a transparent material. Each of the at least one fluid channel includes a separation portion, a waste arm portion, a first sample arm portion, and a second sample arm portion. In one embodiment, the first sample arm portion is adapted to receive a biasing solution and the second sample arm portion is adapted to receive the sample of biomolecular analyte. In another embodiment, the at least one fluid channel includes a microfluidic channel. The transparent test module can be formed from glass, from a polymer, a co-polymer, or any combination of these.

In another aspect, the invention features a method of determining center channel locations in a transparent test module including a plurality of separate fluid channels disposed therein. The method includes: providing a transparent test module including the plurality of separate fluid channels, each of the separate fluid channels having a front end position, a center channel position, and a known channel width; scanning over a portion of the transparent test module including each of the plurality of separate fluid channels with a light beam to generate a reflected light beam; collecting the reflected light beam with a light detector to generate a waveform of intensity through the portion of the transparent test module including each of the plurality of separate fluid channels; eliminating peaks determined not to be associated with the plurality of separate fluid channels; identifying a location within the waveform of the front end position for each of the plurality of separate fluid channels; identifying all remaining peaks along the waveform within a first distance extending from each of the identified front end positions; and determining the center channel positions of each of the plurality of separate fluid channels from an average of locations of all of the remaining peaks within the first distance from each of the identified front end positions.

BRIEF DESCRIPTION OF THE DRAWINGS

The foregoing and other features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIGS. 20A-20C are sequence listings of a known HIV amplicon (SEQ ID NO:1), unedited data generated from a nucleic acid analyzing device of the present invention (SEQ ID NO: 2), and edited data generated from the nucleic acid analyzing device of the present invention (SEQ ID NO: 3), respectively. For formatting purposes, FIG. 20A is spaced over two pages FIG. 20A-1 and FIG. 20A-2.

DETAILED DESCRIPTION

There is a compelling need for a ruggedized DNA separation device that can analyze samples reliably and quickly in the field (i.e., non-laboratory use). Traditional approaches to ruggedizing DNA separation devices have included adding bulky cushioning and/or structural support members. These approaches have not met industry's needs for a number of reasons including: the non-portability of the devices due to the extra weight of the cushioning and/or structural support members, the unreliability of device results due to an increase in background noise generated by uncontrolled vibrational forces acting upon sensitive equipment, and the inherent high power consumption rates needed for conventional devices.

Figure 1A:
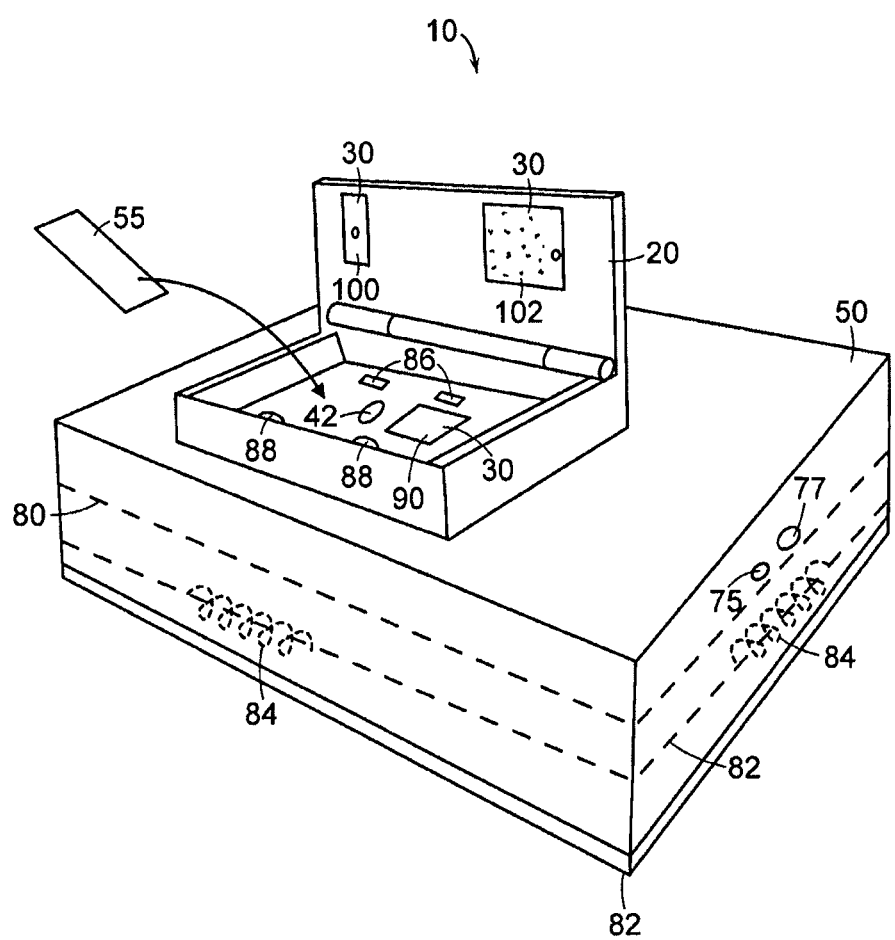
FIG. 1A is a perspective view of a portable system for processing biomolecular analyte according to the invention. A sample holder of the portable system is shown in an open position.
Figure 1B:
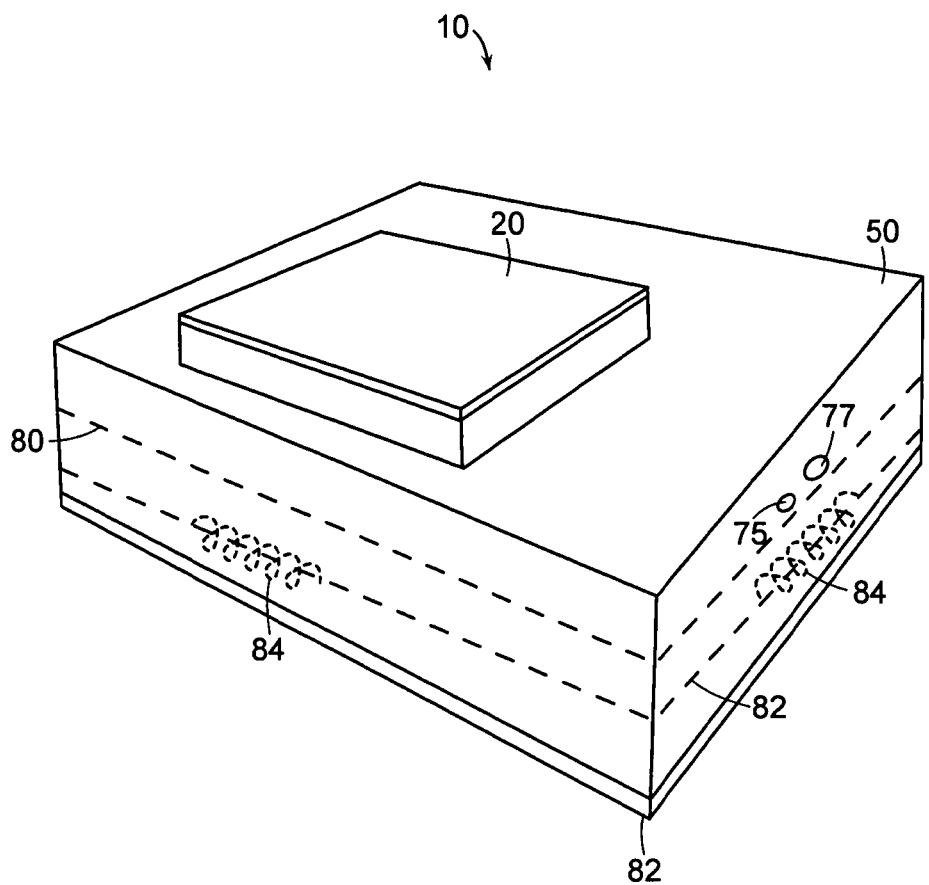
FIG. 1B is another perspective view of the portable system of FIG. 1A. The sample holder of the portable system is shown in the closed position.
Figure 2:
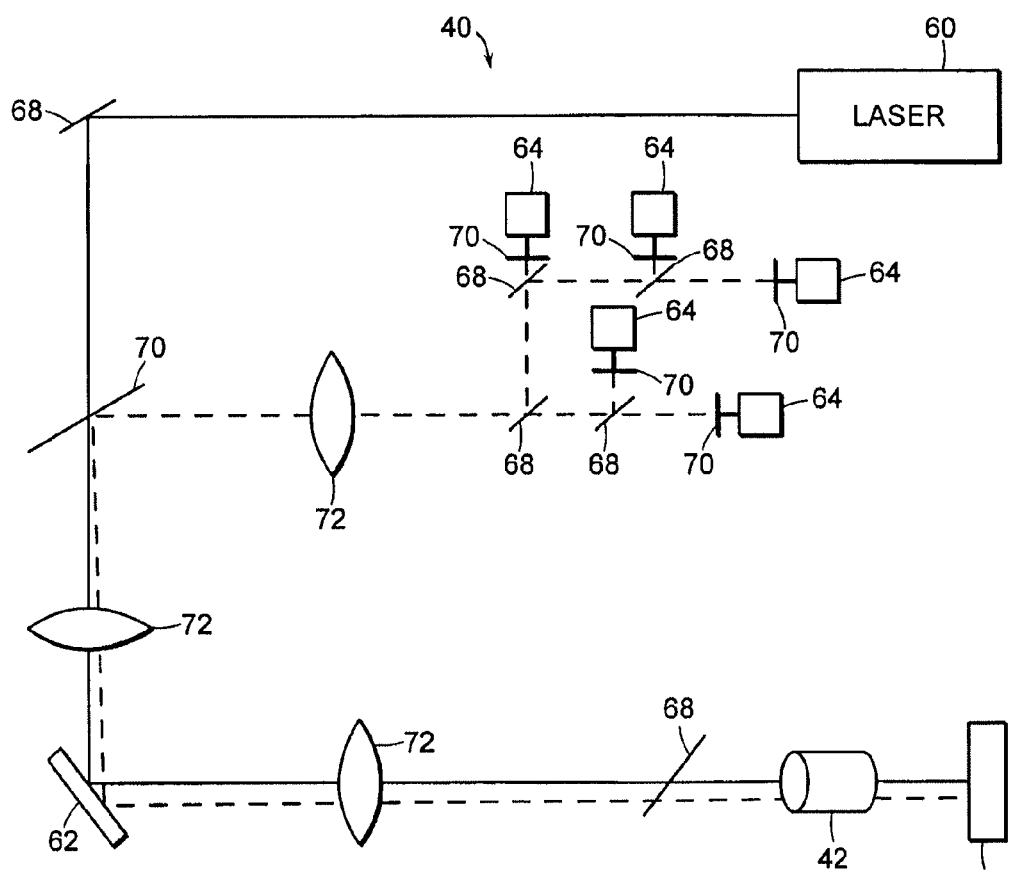
FIG. 2 is a schematic view of a laser excitation and fluorescence detection system used within the portable processing system of the present invention.

In contrast to traditional approaches, an embodiment of the invention is directed to a ruggedized DNA separation/sequencing device (e.g., a device that can be mounted in a mobile forensic unit) used to analyze biomolecular analyte. In general, the invention provides fast, reliable separation and sequencing analysis out in the field. Referring to FIGS. 1A, 1B, and 2, the ruggedized separation device 10 includes a sample holder 20, an electrophoresis assembly 30 connected to the holder 20, and a fluorescence excitation and detection system 40 (see FIG. 2) located underneath the sample holder 20 and covered by protective cover 50 (see FIG. 1A). The fluorescence excitation and detection system 40 includes an opening 42 within the holder 20 so that an energy source that induces fluorescence (e.g., a laser beam) and the resulting induced fluorescence can pass between the holder 20 and the fluorescence excitation and detection system 40.

Another embodiment of the invention is directed to non-controlled or semi-controlled environments such as police department offices, mobile forensic labs, physician's offices, hospital laboratories, clinical laboratories and other points of care locations. In such settings non-skilled or semi-skilled operators must be able to operate and maintain the devices at low cost and with little to no training or experience required. In addition, these settings may be in environmental locations where ambient conditions vary significantly. The devices must be able to withstand temperature and other environmental fluctuations without affecting results. One aspect of this is the ability to sustain shock and vibration without the need for realignment or re-initialization. Furthermore, in many of these environments there is a need for rapid and accurate results while the patient is still with a user of the device (e.g., a treating physician, a police detective, a forensic scientist, or other user). For example, devices in accordance with the present invention can be used by an infectious disease physician during an examination to select an appropriate antibody therapy to give to a sick patient, or by a oncologist surgeon to make an intra-operative diagnosis in a cancer patient.

The sample holder 20 receives and supports a test module 55 including a plurality of separate microchannels. Samples of biomolecular analyte are injected into the microchannels and then the test module 55 is placed within the holder 20 for analysis. After inserting the test module 55 into the holder 20, a user places the holder 20 in a closed position (see FIG. 1B) so that the electrophoresis assembly 30 makes contact with the test module 55. With the holder 20 in the closed position, the user activates the electrophoresis assembly 30 to apply a voltage to the test module 55 so that components consisting of biomolecular analyte (e.g., STRs) separate.

The size of each component within or attached to device 10 can be miniaturized by any one or a combination of the following factors: changing the type of energy source used to induced fluorescence, varying the size of the chip, reducing power consumption needs, reducing the size of the electronics and incorporating sample preparation into the unit. For example, a small aliquot of blood can be introduced into one port of the device and routed to a sample preparation area for DNA extraction. The resulting DNA sample then may be manipulated and analyzed by the microfluidic chip as described elsewhere in this specification.

The fluorescence excitation and detection system 40 excites the components separated by electrophoresis of a DNA sample (e.g., STRs) by scanning an energy source (e.g., a laser beam) through a portion of each of the microchannels while collecting and transmitting the induced fluorescence from the biomolecular analyte to one or more light detectors for recordation and ultimately analysis. In one embodiment, the fluorescence excitation and detection assembly 40 includes a laser 60, a scanner 62, one or more light detectors 64, and various mirrors 68, filters 70 (e.g., band-pass filters, dichotic filters), and lenses 72 for transmitting a laser beam emitted from the laser 60 through opening 42 to the test module 55 and back to the light detectors 64. The scanner 62 moves the incoming laser beam to various scanning positions relative to the test module 55. Specifically, the scanner 62 moves the laser beam to a pertinent portion of each microchannel within the test module 55 to detect respective separate components. The one or more light detectors (e.g., photomultiplier tubes, photodiodes, CCD cameras or linear array detectors) 64 collect data (e.g., the fluorescent DNA/STRs signal) from the test module 55 and provide the data electronically through a cable attached to port 75 to a data acquisition and storage system located outside the protective cover 50. In one embodiment, the data acquisition and storage system can include a ruggedized computer available from Option Industrial Computers (Baudreuil-Dorion, Quebec, Canada).

Uncontrolled vibrations that interact with the fluorescence excitation and detection system 40 can be detrimental to data collection and ultimately lead to problems with obtaining reliable results. These problems can be exacerbated when a DNA separation/sequencing device is used in an uncontrolled environment, such as when the device is transported and used at a crime scene (i.e., field use). To reduce the effects of environmental vibration, the present invention includes one or more of the following various elements. These elements each have a minimal impact on the overall weight or bulk of the device and thus, allow for the device of the present invention to be easily transported (i.e., portable). For example, in one embodiment, the fluorescence excitation and detection system 40 resides on a plate 80 formed from a single piece of material (i.e., unitary construction). That is, the laser 60, scanner 62, the one or more light detectors 64, the mirrors, 68, filters 70, and the lenses 72 are secured to plate 80 made from a single piece of material, such as, for example a single piece of aluminum. As a result, all the components of the fluorescence excitation and detection system 40 have a common base that has no joints or other intersections that could potentially transmit and or generate vibrations to the fluorescence excitation and detection system 40. The components of the fluorescence excitation and detection system 40 are secured to the single plate 80 with one or more fasteners commonly used in the optics industry. In addition to using the fasteners, some embodiments of the invention also include securing elements for further reducing the rotational movements of these components during use. Since each of the components of the fluorescence excitation and detection system controls some portion of the laser beam's path, any movement of the components can cause a disturbance in data collection. As a result of these disturbances, the data flow can be interrupted or corrupted, thereby producing unreliable results. The securing elements, which can be attached to the plate 80 prior to the installation of the components thereover, extend vertically away from the plate 80 and fit into openings created in the components to limit the components' rotational movement thereof during use. For example, in one embodiment, the securing elements comprise dowel pins extending from the plate 80. The components of the fluorescence excitation and detection system 40 are positioned on to the plate 80 such that apertures in the components fit snuggly over the dowel pins to limit the rotation of the components. To hold the components to the plate 80, fasteners, such as, for example, screws are used to connect the components to plate 80.

Figure 1C:
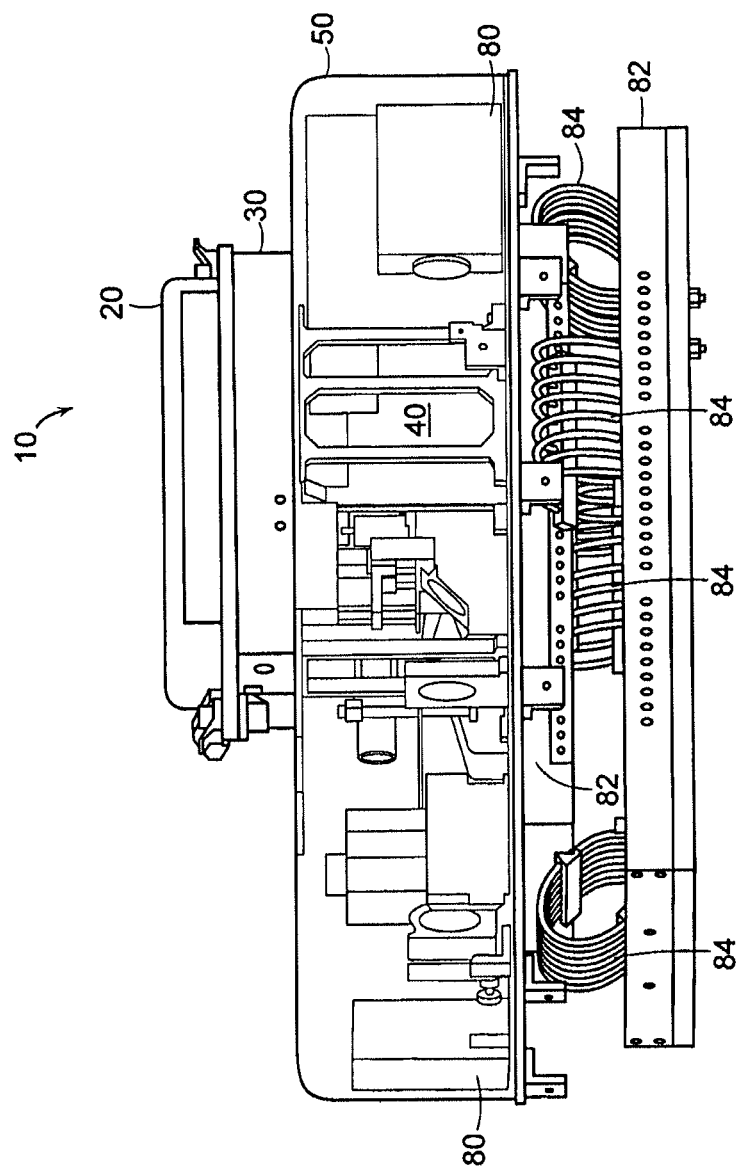
FIG. 1C is a side view of the portable system of FIG. 1A. A portion of a cover has been removed so that a portion of the interior of the portable system is visible.

As a further example of how vibration and shock can be controlled in the present invention, some embodiments include one or more damping devices positioned between the ground and the plate 80 supporting the fluorescence excitation and detection system 40. These damping devices absorb vibrational forces and reduce the transmission of vibrations to the fluorescence excitation and detection system 40. For example, in the embodiment of the invention shown in FIGS. 1A, 1B, and 1C, the device 10 includes a frame 82 that supports the plate 80. Disposed between the frame and the plate 80 are four damping coils 84 (two of which are in view in FIGS. 1A and 1B, four in FIG. 1C) that absorb shock and other forces, thereby preventing or substantially reducing transmission of vibration to the fluorescence excitation and detection system 40. The damping coils 84 in the embodiment shown in FIGS. 1A and 1B are positioned to equally balance the weight of the device. That is, each coil 84 supports an equal amount of weight. In other embodiments, the damping coils 84 can be positioned symmetrically about the frame 82 or can be positioned as desired. Moreover, more or less than four damping devices can be used to absorb shock. Examples of suitable damping devices for controlling shock and vibration include coils of wire rope isolators (e.g., stainless steel wire rope available from Enidine of Orchard Park, N.Y.) or metal springs having a large stiffness coefficient, pneumatic or hydraulic shock absorbing mounts, and rubberized shock absorbing mounts.

In some embodiments, automated locking features are used to reduce motion of the test module 55 during analysis. For example, in certain embodiments of the present invention, the holder 20 can further include non-moveable test module stops 86 and automated positioning bumpers 88. The automated positioning bumpers 88 move towards the non-moveable stops 86 as the top portion of the holder 20 is closed. Thus, the automated positioning bumpers 88 guide and push an inserted test module 55 up against the non-moveable test module stops 86. As a result, the test module 55 is positioned snuggly between the test module stops 86 and the automated positioning bumpers 88, thereby locking the test module in place and reducing lateral movements of the test module during analysis.

All of the features described above can be used alone or in combination to provide shock absorption and prevent vibration transmission to the fluorescence excitation and detection system 40 without adding excess weight to destroy ruggedized nature and/or the small, miniaturized size of the device 10.

Other features of the present invention also contribute to the ruggedized nature of the device 10. For example, the laser 60 used within the fluorescence excitation and detection system 40 can be selected to emit a large amount of power while using little energy. As a result, reliable measurements can be made and detected by using laser 60, while not requiring a large amount of power from an external energy source connected to the device 10 through port 77. In general, conventional, stationary devices, such as the type used in laboratories, use gas lasers (e.g., helium-neon lasers). These gas lasers require a large amount of energy to lase properly. For example, a typical gas laser draws about 20 to 30 amps at 240 volts (i.e., requiring 7,200 W of power and having a maximum power consumption of about 2.5 kVA or greater). Thus, a portable energy source connected to this type of laser would have to be of a size large enough to support this power usage. In general, solid state lasers require less energy and are more efficient than their gas phase laser counterparts, and thus contribute to the portability and ruggedized nature of the present invention. An example of a laser which requires limited power for proper operation and is suitable for use with the present invention is a solid state laser, such as, for example, a diode pumped solid state laser. Typically, diode pumped solid state lasers use less than 2 amps at 240 volts (i.e., a power use of 480 W and having a maximum power consumption of less than 1.5 kVA and in some cases, less than 0.5 kVA). In some embodiments, lasers or other light sources that draw less than 10 amps at 240 volts can be used without reducing the portability of device 10. For example, a light source that draws less than 10 amps at 240 volts uses less than 3,000 W of power. These light sources can be powered by a small portable energy source (e.g., a 6,000 W or less power supply; a 1.5 kVA or less maximum power consumption power supply), thereby preserving the miniaturized nature of the present invention. In one embodiment of the present invention, the light source comprises a solid state, such as a Sapphire 488 HP (Santa Clara, Calif.) solid state laser, which has a maximum power consumption of 0.75 kVA. In addition, the Sapphire solid state laser can withstand 7 g of lateral and 15 g of vertical shock. As one skilled in the art will appreciate, any laser with the desired optical properties can be used within the teachings of the present invention.

A thin thermofoil heater 90 disposed within the holder 20 also contributes to the portability of device. The heater 90 is situated within holder 20 to be in thermal contact with an inserted test module 55. This design allows the dimensions of the heater 90 to be small and equivalently sized with the test module 55. The heater 90, which may be activated through a remote controller located outside of the device 10, can be used to apply thermal energy to the test module 55. The heat applied to the test module 55 aids in separation of the biomolecular analyte (i.e., the heater 90 is part of the electrophoresis device 30). The use of the small thermofoil heater 90 in combination with the test module 55 (e.g., a planar microfluidic chip) allows for efficient heat transfer between the heater 90 and the test module 55. As a result, a large reduction in the amount of electric energy or power consumption required to heat the test module and to maintain improved temperature control is achieved. In conventional capillary electrophoresis systems, heating and temperature control of the capillaries is achieved by placing the capillaries in an oven. The large volumes of the ovens and inefficient heat transfer between the oven heater elements and the capillaries results in the need for a large amount of energy, which could be potentially draining on a portable energy source and/or require a larger power supply, thereby decreasing the portability of the nucleic acid separation/sequencing device. As a result, the present device can be serviced by an attached, small, portable energy source (e.g., 6,000 W or less and/or a 1.5 kVA or less maximum power consumption) for significant time periods, thereby increasing the portability of the present invention.

In addition to aiding in separation of the biomolecular analyte, the heater 90 also contributes to obtaining high resolution results. For example, the intimate contact between the heater 90 and the test module 55 provides efficient heat transfer there between. As a result, the heater can maintain the temperature of the test module 55 within ±1 degree C. of a desired temperature setting, thereby minimizing any detrimental environmental temperature effects.

Separation or electrophoresis of the biomolecular analyte occurs within the microchannels in the test module 55. In general, the test module 55 is made from a transparent material that allows at least a part of the energy source inducing fluorescence (e.g., laser beam) from the fluorescence excitation and detection system 40 to transmit through the test module 55 to interact with the sample located therein. Examples of suitable transparent materials include glasses (e.g., aluminosilicate glass, borosilicate glass, fused silica glass, and soda lime glass), single crystal alumina, and clear polymers or copolymers (e.g., polymethyl methacrylate, uv treated polycarbonate, or cyclic olefin copolymer).

Figure 3A:
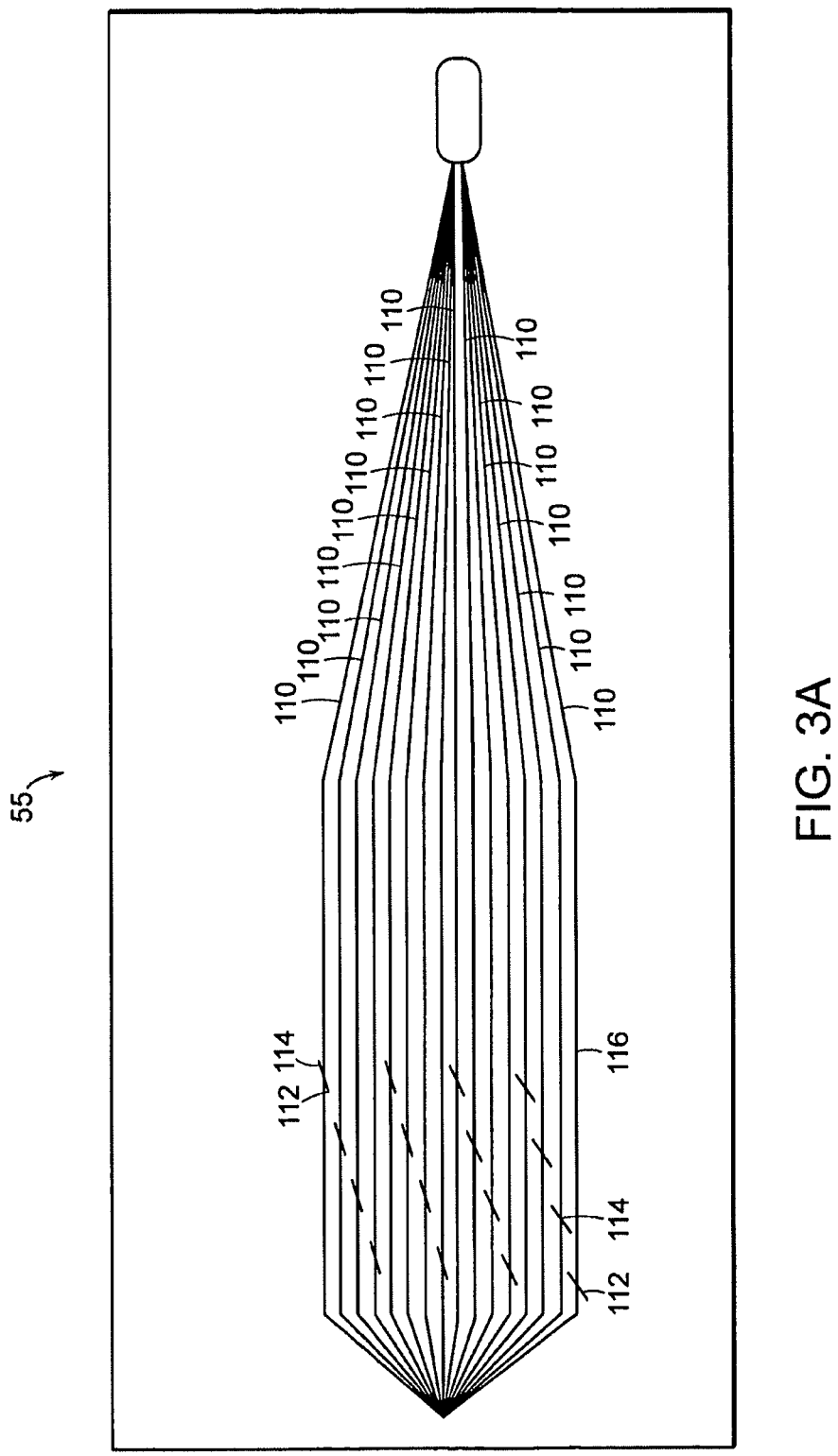
FIG. 3A is a top view of a test module that is usable in the systems of FIGS. 1A and 1B.
Figure 4:
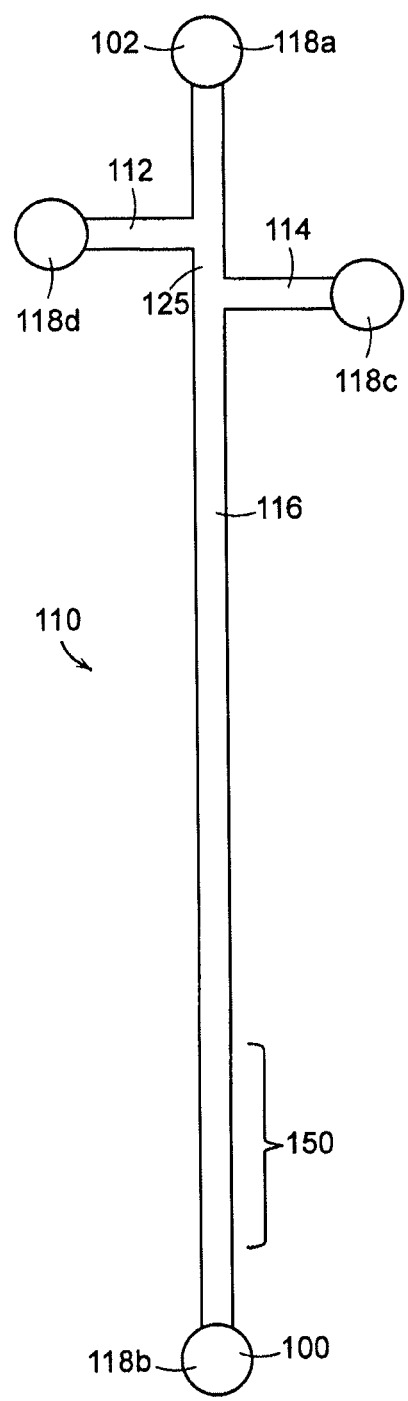
FIG. 4 is a schematic view of a channel usable in the test module of FIG. 3.

Referring to FIGS. 3A and 4, one or more microchannels 110 (16 channels are shown in FIG. 3A, and one channel is shown in FIG. 4) each include a sample arm 112, a waste arm 114, and a separation channel 116. The microchannels 110 can be manufactured on a transparent plate by utilizing standard photolithography and chemical etching procedures to make channels having a depth of about 20 to 100 microns and a width of about 40 to 2,000 microns. In one embodiment, the preferred channel depth is about 40 microns and the preferred channel width is 90 microns. As shown in FIG. 4, sample and waste arms 112 and 114 are offset from one another at a distance of about 50 to 1,000 microns along a length of the separation channel 116. In one embodiment, the sample and waste arms 112 and 114 are offset from one another at a distance of 500 microns along a length of the separation channel 116. Openings 118 (e.g., 118a, 118b, 118c, 118d) to insert samples and remove waste as well as to make electrical connections to the anode 100 and the cathode 102 are laser drilled into the transparent plate. For example, in one embodiment, a plate including 16 microchannels includes 16 sample holes, 16 waste holes, 1 or more anode holes and 1 or more cathode holes. In another embodiment in which includes multiple test modules 55 (e.g., 10 test modules each having 16 microchannels) formed on a single transparent plate includes 160 sample holes, 160 waste holes, 160 anode holes and 160 cathode holes. In still yet another embodiment, which includes two sample arms 112a and 112b per microchannel, a plate is laser drilled to include 32 sample holes, 16 waste holes, 1 or more anode holes, and 1 or more cathode holes per test module 55. These microchannel structures are patterned and etched into a transparent plate by traditional semiconductor fabrication processes. Following the patterning, ports for accessing the channels are formed by drilling processes, including laser drilling, abrasive jet drilling, and ultrasonic drilling. The etched transparent plates are then cleaned with multiple cleaning processes to remove debris and surface contamination.

To close and seal the channels 110 so that they can be filled with biomolecular analyte, the etched transparent plate is thermally bonded to a blank or non-etched transparent plate. The bonding process is performed in an oven in a two step process. The two step bonding process includes positioning the two transparent plates (i.e., one etched and one non-etched) in the oven with the non-etch plate covering the etched surface of the etched plate so that a seal forms at all points including in between the etched microchannels. The transparent plates are heated to a temperature less than about 200 C for about 120 minutes. A force of about 0.5 to 10 pounds is uniformly applied to the plates throughout the heating process to promote the thermal bond. Upon completion of the above low temperature heating process, the bonded transparent test module 55 is visually inspected. If there are no apparent cracks or other damage, the bonded transparent test module 55 is heated in a high temperature oven at a temperature of about 735 degrees C. to complete the seal. The above thermal bonding process is further described in Semiconductor Wafer Boding: Science and Technology by Q.-Y. Tong and U. Gosele, published by Wiley Publishers, November 1998, which is hereby incorporated by reference in its entirety.

Figure 3B:
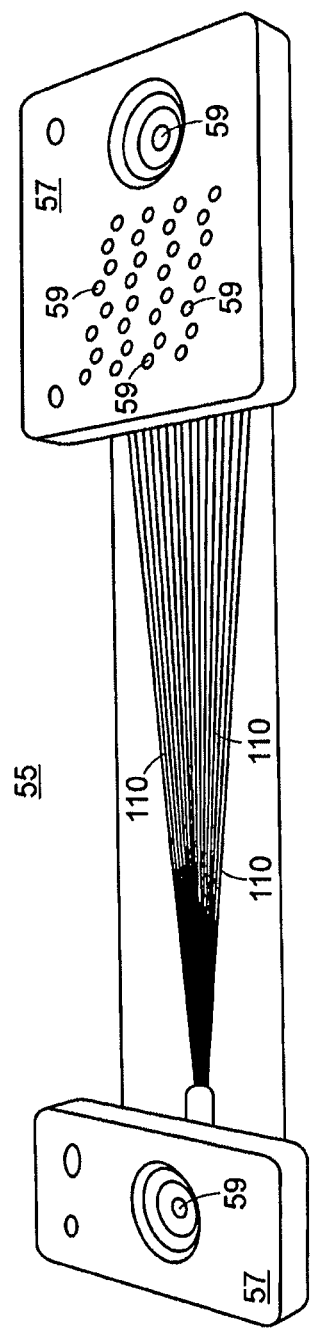
FIG. 3B is another top view of a test module that is usable in the systems of FIGS. 1A and 1B. The test module shown in this figure includes an attached sample board for holding samples and fluids to be injected into the test holder.

Referring to FIG. 3B, in certain embodiments, the test module 55 includes a sample board 57 attached to a top surface including the openings to the etched microchannels. The sample board 57 includes a number of reservoirs 59 for holding samples and fluids used in electrophoresis. In addition to serving as a holder for fluids, the sample board 57 also aids in providing proper alignment of the test module 55 in the holder 20. For example, the reservoirs 59 are positioned within the sample board 57 to provide alignment and registration of the reservoirs and the electrodes of the electrophoresis assembly 30 when the test module 55 is inserted into the holder 20.

Once the test module 55 is sealed, the internal surfaces of the channels are treated to prevent electroosmosis and sample-wall interactions using a slightly modified Hjerten protocol as described by Luba Mitnik et al. in *Electrophoresis* 2002, volume 23, pages 719-26, hereby incorporated by reference in its entirety. The channels are filled with a sieving matrix material and the openings leading the channels are filled with either a buffer solution or deionized water. The openings 118 are sealed and the test module 55 is stored until it is needed for use (i.e., until the test module is needed to hold a sample of biomolecular analyte for analysis).

When one or more samples are ready to be analyzed the seal on the test module 55 is removed and the buffer solution or deionized water is removed from each of the openings leading to channels 110 etched into the test module 55. To condition the channels for use, the openings to the channels 110 are flushed with deionized water three times. Each time the water is removed by aspiration until dry. An electrophoresis gel or sieving matrix/material is injected into each of the channels with a syringe. As one skilled in the art will appreciate, a variety of sieving materials may be used. An example of a suitable sieving material is a high molecular weight linear polyacrylamide (LPA), such as, for example, a high molecular weigh 4% LPA commercially available from Dakota Scientific (Sioux Falls, S. Dak.). Examples of other suitable sieving materials are described by Methal. et al., in "Polymeric Matrices for DNA Sequencing by Capillary Electrophoresis" in *Electrophoresis* 2000, Vol. 21, pages 4096-4111 and by Ruiz-Martinez in "DNA Sequencing by Capillary Electrophoresis with Replaceable Linear Polyacrylamide and Laser-Induced Fluorescence Detection," in *Anal. Chem.*, Vol. 65, pages 2851-58, 1993, both disclosures of which are hereby incorporated by reference in their entirety.

The channel is filled with three times the volume of the channel worth of sieving gel from the anode opening 118b first and then three times the volume of the channel worth of the sieving gel from the cathode opening 118a to coat the microchannel 110 completely with the gel and ensure that all water has been removed. The openings 118 at the anode 100 (i.e., opening 118b), the cathode 102 (opening 118a), and the waste arm 114 (opening 118c) are then filled with a buffer solution and the opening 118d of the sample arm 112 is filled with deionized water.

To complete the conditioning of the microchannels, the test module 55 is inserted into the holder 20 and the holder 20 is closed so that the cathode 102 and anode 100 connections on the holder 20 interface with the cathode opening 118a and anode opening 118b on the test module 55. A first biasing configuration is applied to the test module 55 to condition the channels in which a voltage of less than about 10 KV is applied across the cathode 102 and anode 100 to move the sieving matrix down the separation channel 116 from the cathode opening 118a towards the anode opening 118b. Then a second biasing configuration is applied to the test module 55 to complete the conditioning. The second biasing configuration includes applying a voltage of less than 4 KV between the sample arm 112 and the waste arm 114 to move the ions from the sample arm opening 118d into the waste arm opening 118c. The test module 55 is removed from the holder 20 and cleaned to remove all of the water and buffer. Each of the ports is rinsed with deionized water at least three times and then the microchannels 110 are visually inspected under magnification to check for the presence of bubbles. The test module 55 is now ready for use. The conditioning processes are performed on the test module at a temperature of between 40 to about 70 degrees C. That is the heater 90 warms the test module to a temperature of between 40 to about 70 degrees C. during the conditioning process. In certain embodiments, the preferred temperature of operation is 50 degrees C.

An operator loads a sample of biomolecular analyte (including a fluorescent dye to mark the STRs) into the test module 55 by injecting a sample or a test control into one or more of the sample openings 118d of the microchannels 110 through the sample board 57. The anode, cathode and waste openings 118 a, 118b, and 118c are filled with the buffer solution. The test module 55 is placed back into the holder 20 and the anode 100 and cathode 102 are connected to the test module 55.

Figure 5:
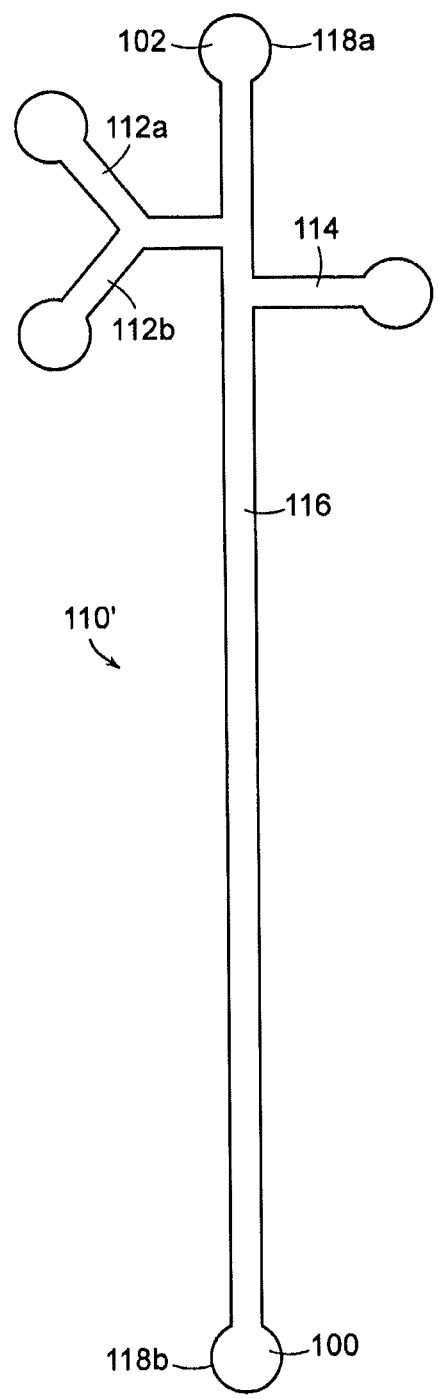
FIG. 5 is a schematic view of another channel usable in the present invention.

In another embodiment of the invention, one or more of the above cleaning steps is eliminated in the conditioning process. Specifically, in certain embodiments of the invention (see FIG. 5), a test module includes at least one microchannel 110 having a separation channel 116, a waste arm 114, and two sample arms 112a and 112b. As a result of including the two sample arms 112a and 112b, cleaning processes used to clean the test module 55 after conditioning is eliminated. That is, the microchannels are cleaned once, prior to adding the sieving matrix. In this embodiment, sample arm 112a is filled with deionized water and sample arm 112b is filled with biomolecular analyte including the fluorescent dye. The microchannel 110 is first conditioned by applying the first and second biasing configurations. Then, the sample of biomolecular analyte is analyzed without having to remove the test module 55 from the holder 20 to clean and prepare the test module 55 for a second run. As a result of adding the second sample arm 112b, a significant savings in processing time can be achieved.

Figure 6:
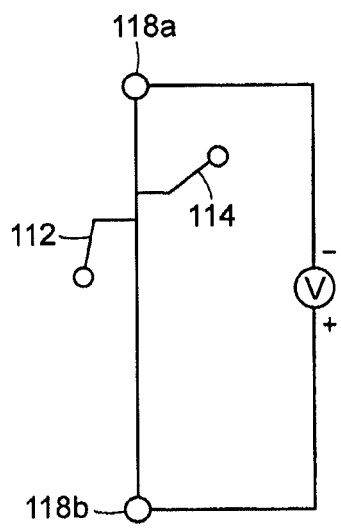
FIG. 6 is a schematic view of an embodiment of a first biasing condition applied to a test module used in the present invention during electrophoresis.
Figure 7:
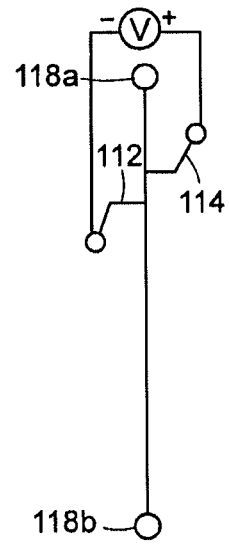
FIG. 7 is a schematic view of an embodiment of a second biasing condition applied to the test module during electrophoresis.
Figure 8:
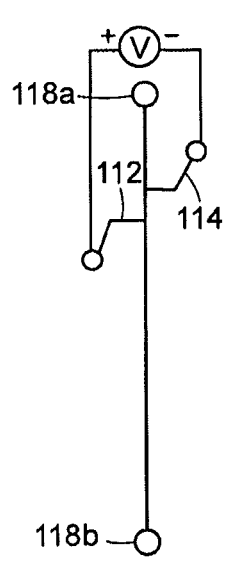
FIG. 8 is a schematic view of an embodiment of a third biasing condition applied to the test module during electrophoresis.
Figure 9:
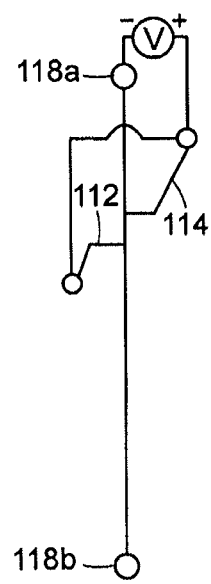
FIG. 9 is a schematic view of an embodiment of a fourth biasing condition applied to the test module during electrophoresis.
Figure 10:
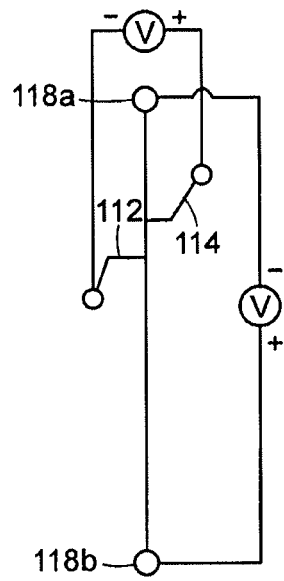
FIG. 10 is a schematic view of an embodiment of a fifth biasing condition applied to the test module during electrophoresis.
Figure 11:
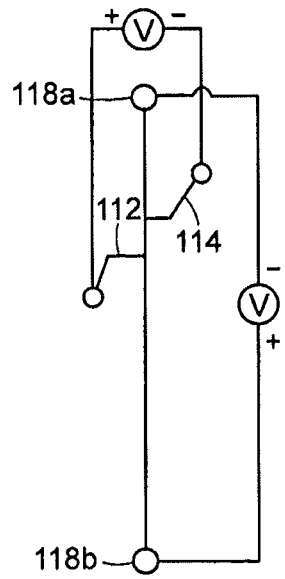
FIG. 11 is a schematic view of an embodiment of a sixth biasing condition applied to the test module during electrophoresis.
Figure 12:
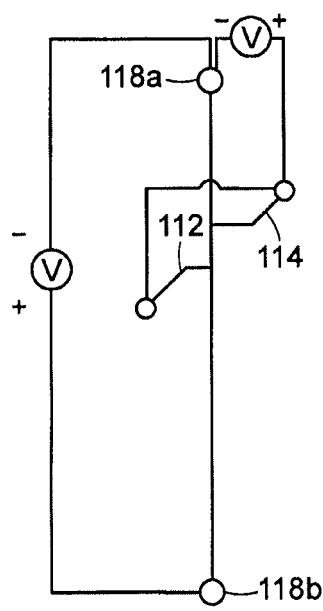
FIG. 12 is a schematic view of an embodiment of a seventh biasing condition applied to the test module during electrophoresis.

To analyze a sample, various electrophoresis procedures can be used to prepare and separate the sample into STRs. One of these procedures involves heating the test module 55 to a temperature of about 40 to about 70 degrees C. while applying a voltage to separate the biomolecular analyte. For example, in one preferred embodiment, the temperature of the test module is held at 50 degrees C. during electrophoresis. Prior to applying separation conditions to the test module 55, at least one biasing condition is applied to each of the microchannels 110 in the test module 55 to prepare the sample for separation. A first biasing condition moves the buffer solution into the separation channel 116 from the cathode opening 118a towards the anode opening 118b. The first biasing condition is represented in FIG. 6, in which a voltage of less than 10 KV is applied between the cathode 102 and the anode 100. A second biasing condition shown in FIG. 7 applies a voltage between the sample arm 112 and the waste arm 114, and moves the analyte from the sample arm 112 towards the waste arm 114. A third biasing condition shown in FIG. 8 applies a voltage from the waste arm 114 to the sample arm 112 to move the analyte from the waste arm 114 towards the sample arm 112. A fourth biasing condition shown in FIG. 9 applies a voltage between the cathode 102 and the waste arm 114 to move the analyte away from the separation channel and back into the sample arm 112 and the waste arm 114. The first biasing condition is applied with a first power supply and the second, third, and fourth biasing conditions are applied with a second power supply. When both the first biasing condition and one of the second, third, or fourth biasing conditions are applied at the same time, further biasing conditions can be applied to the microchannel 110. For example, as shown in FIG. 10, a fifth biasing condition, which is a combination of the first and second biasing conditions, moves the analyte from the sample arm 114 towards the waste arm 114, while also moving the analyte in the separation channel 116 from the cathode 102 towards the anode 100. A sixth biasing condition is formed by the combination of the first and third biasing conditions and is shown in FIG. 11. A seventh biasing condition, shown in FIG. 12, is a combination of the first and fourth biasing conditions. The seventh biasing condition moves the analyte in the area of intersection between the separation channel and the sample and waste arms (e.g., intersection region 125) towards the sample and waste arms 112 and 114, while also moving the analyte in remaining or other portions of the separation channel 116 from the cathode 102 towards the anode 100.

Sequential application of the above biasing conditions allows for a number of different functions including loading, stacking, separation, and prevention of excess analyte from diffusing into the separation channel during separation. Electric fields of between about 50 to about 500 V/cm are typically applied across the cathode 102 and the anode 100, while electric fields of about 50 V/cm to about 500 V/cm are applied to the waste and sample arm openings 118d and 118c. Loading of the analyte into the separation channel 116 is accomplished by applying the second bias configuration together with an electric field of about 50 V/cm to about 400 V/cm for 0.5 to 5 minutes about the sample and waste arms 112 and 114. Stacking of the analyte at the intersection region 125 is accomplished by applying the first bias configuration together with an electric field about the channels 110 of up to about 500 V/cm for a relatively short time frame (e.g., about 1 second to about 10 seconds). The conductivity difference between the intersection region 125 and the separation channel 116 forces the analyte in the intersection region 125 to form a compressed band, which allows for high resolution separations. Separating the analyte is accomplished by applying the first biasing configuration together with an electric field of about 50 to about 500 V/cm to move the compressed band of analyte towards the anode 100 from the cathode 102. The first biasing configuration is applied to the compressed bands until the largest fragments of interest have moved through a detection zone 150 (i.e., a portion of the separation channel which interacts with the laser beam). Analyte from the sample arm 112 and waste arm 114 can diffuse into the separation channel 116 leading to distortions in the electrophoregram baseline and a reduction in a signal to noise ratio. As a result, excess analyte in the sample arm 112 or waste arm 114 is prevented from entering the separation channel 116 during analysis by applying the seventh biasing configuration to ensure that a negative electric field is setup between the cathode opening 118a and each of the sample and waste openings 118d and 118c, respectively. In some embodiments of the invention, the seventh biasing configuration as described above is applied for the remainder of an analysis to ensure the quality of the signal collected by the fluorescence excitation and detection system 40. In other embodiments, once the conduction bands have moved away from the intersection region 125 towards the detection zone 150, the seventh biasing condition is switched off and the first biasing condition is applied. In this embodiment, excess analyte is unable to diffuse into the separation channel 116 because the conduction bands have moved away from the intersection region 125. As a result, excess analyte cannot interfere with data collection. In another embodiment, excess analyte is prevented from entering the separation channel 116 by removing analyte from the sample opening 118d and/or waste opening 118c during separation. Either the third or the fourth biasing configuration can be applied during separation to move excess analyte to either the sample arm 112 or a combination of the sample and waste arms 114 for removal.

Once the biomolecular analyte sample is separated, biasing configurations are applied to move the separated components (STR loci) towards the detection zone 150. The laser beam emitted from the laser 60 scans through the detection zone 150 and the induced fluorescent light from the DNA is collected and transmitted by the light detectors 64 within the fluorescence excitation and detection system 40. As the laser beam scans through the detection zone 150, laser light is absorbed by the fluorescently tagged STR loci that are moving therethrough. The induced fluorescence from each of the tagged STR is collected by the fluorescence excitation and detection system 40 and transmitted to the detectors 64. Through a combination of dichroic mirrors and band-pass filters, the emission wavelength of the specific fluorescently tagged and hence the specific STRs are identified. These results can be compared to industry standards or other samples for forensic identification purposes.

In the present invention, a novel "lanefinding" process is used to automatically compensate for changes in chip position or other misaligned elements in the optical train without requiring the user to perform a realignment procedure. In some embodiments, "lanefinding" is included as one of the components used to ruggedized apparatus described herein.

Alignment issues between the fluorescence excitation and detection system 40 and the test module 55 can introduce degradation in signal quality, specifically the relative intensity level of the induced fluorescence relative to a background noise level. "Lanefinding" is process used in some embodiments of the present invention to maximize the signal to noise ratio of the fluorescence data from the STRs and to more accurately find the detection zone 150. Specifically, if the alignment between the excitation energy source and the channels within the test modules 55 is poor, tagged DNA moving through the detection zone 150 will not be efficiently excited. In addition, other regions of the chip, such as, for example, from between the channels, will be excited and thus will result in the generation of excessive background fluorescence. Misalignment between the excitation energy beam and the channel will also result in the collection of excessive background fluorescence relative to the reduced induced fluorescence from the DNA, thereby reducing the signal to noise ratio. As a result of sampling data from other regions other than the detection zone 150, unreliable and/or unusable results are produced. The alignment between the fluorescence excitation energy beam and the detection zone can be monitored and corrected by an attached processor, such as an attached computer running software with the lanefinding program running thereon.

Figure 13:
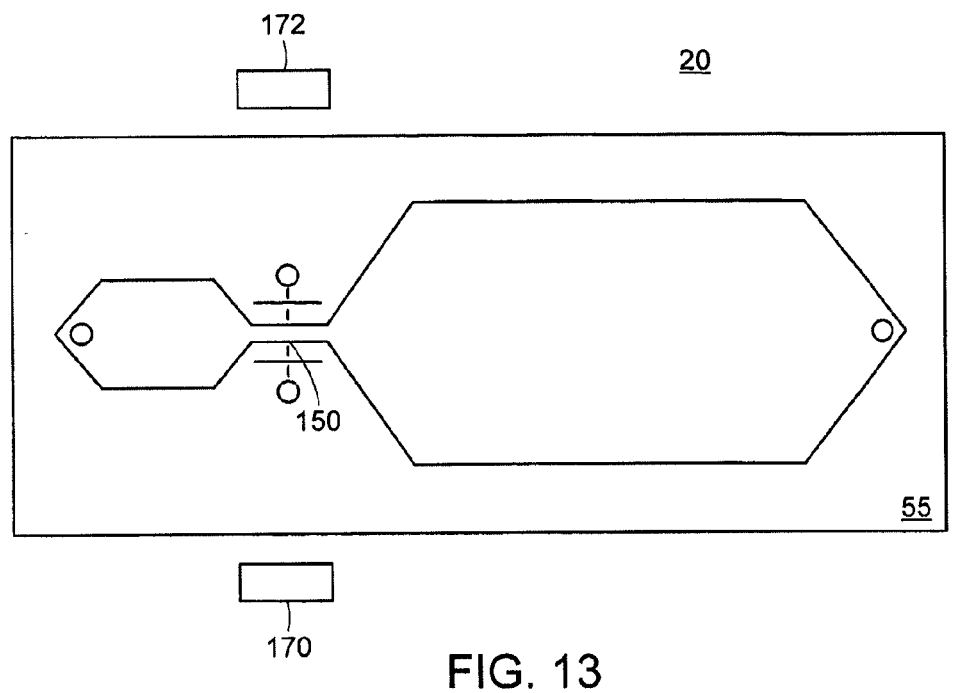
FIG. 13 is a schematic view of an embodiment of a test module disposed within a portion of a holder.
Figure 14:
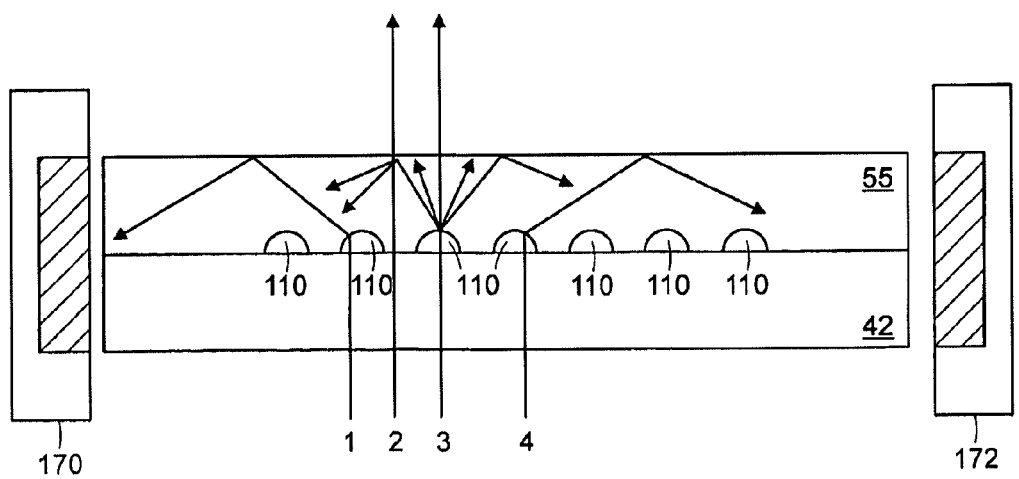
FIG. 14 is an illustration of laser beam paths through a test module.
Figure 15:
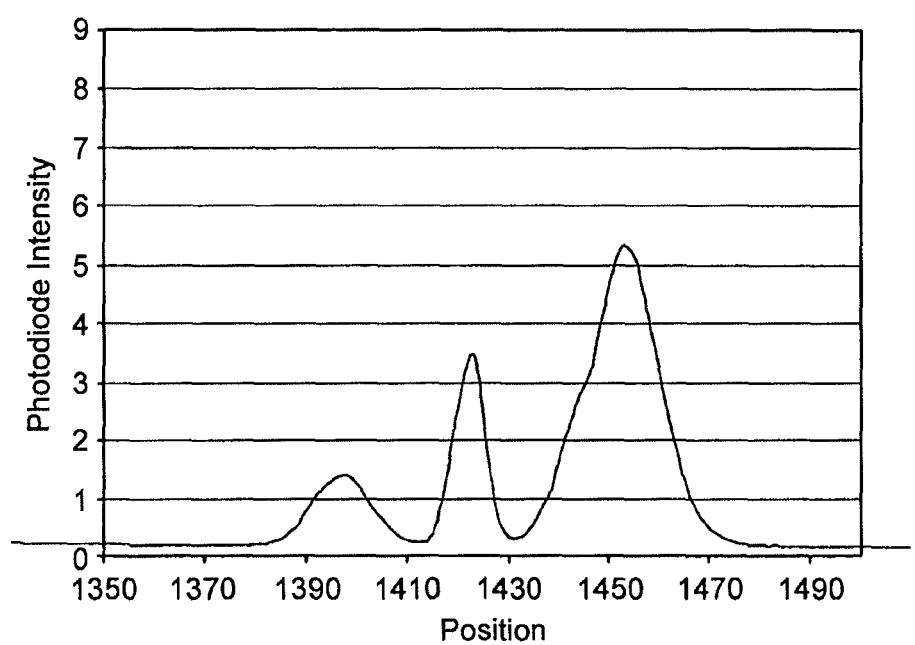
FIG. 15 is a graph of light intensity versus position across a channel of a test module.

Unlike prior art devices, the devices of the present invention are designed to incorporate removeable test modules 55 or chips. In the present invention, some embodiments use novel lanefinding methods to determine the location of each microchannel 110 after initial insertion or removal and re-insertion of a test module 55. Lanefinding eliminates the need for manual re-alignment of the plurality of optics within the fluorescence excitation and detection system 40 when test modules 55 are removed and/or reinserted. In one embodiment, lanefinding removes spurious peaks introduced from aberrations, including without limitation, aberrations caused by scratches or other imperfections in the transparent test module 55, and the presence of foreign particles in the transparent test module 55 and the like. Referring to FIG. 13, the excitation energy source (e.g., laser beam) is scanned through the detection zone 150 on a particular test module before using device 10 to analyze a sample. As the laser beam passes through each channel 110 it is deflected by index of refraction discontinuities between the transparent material between the channels 110 and the medium within the channels. The deflected light beam can scatter and/or waveguide through the test module 55 and can be detected by photodiodes 170, 172 placed on either side of test module. Referring to FIG. 14, there are four general cases where laser light incident on the channels is deflected towards and detected by the photodiodes. As shown in FIG. 14, laser path one intercepts a front edge of a channel and is deflected towards photodiode 170. Laser path two does not intercept a channel, but rather travels only through the transparent material of the test module. As a result, no light is directed towards either photodiode 170 or 172. Laser path three intercepts the center or middle of a microchannel. As shown in FIG. 14, laser beam in laser path three is directed towards both photodiode 170 and 172 and is thus the best location to detect data. Finally, laser path four intercepts a back edge of a channel and is reflected towards photodiode 172 only. FIG. 15 shows a typical waveform at photodiode 172 as the laser beam scans across one microchannel. The waveform shows that the front edge position of the channel 110 is located at about 1385 counts, the middle position is located at about 1425 counts, and the back edge of the channel 110 is located at 1475 counts.

In one embodiment, the lanefinding software determines the position of the middle of each channel 110 by a series of steps designed to eliminate spurious peaks and to identify the front and back edge position of each microchannel 110. In this embodiment, the intensities of the peaks from all of the channels detected by the photodiodes 170 and 172 is normalized to a maximum value of one. At least three scans of the detection zone are recorded and a three-point boxcar average is performed to smooth out the collected data and to smooth out the traces to ensure interpretation accuracy. All peaks within the detection zone 150 are identified and any peak not identified on both waveforms collected by photodiode 170 and photodiode 172 is eliminated. The remaining peaks are reviewed for spurious peaks introduced by aberrations, such as, for example, aberrations caused by scratches or other imperfections or foreign particles in the transparent test module 55. The peaks resulting from these flaws or scratches are identified by examining the space between each peak. As shown in FIG. 15, each of the peaks associated with a particular channel are spaced at regular intervals corresponding to the front, middle and back positions of the channel. That is, each peak is located within a one-third channel width distance apart from each other. Thus, any peak that is not correlated to other peaks with a one-third channel width distance there between is eliminated from the waveform. All remaining peaks are used to determine the middle position of each channel 110.

In one embodiment, the middle position of the channels are determined by first identifying the first peak in the waveform. This peak is identified as the front edge of the first channel. Peaks within 1.2 channel widths from the front edge are identified. These identified peaks are averaged to determine the middle position of the first channel. The next peak located along the waveform at a distance greater than 1.2 channel widths from the first peak is identified and labeled the front edge of the second channel. Peaks within 1.2 channel widths from the front edge of the second channel are identified and averaged together to determine a middle position of the second channel. This process of identifying the front edge and middle position is continued until all channels with the test module 55 are identified. The middle positions of each channel are averaged together to determine an average offset from the front edge position of the channels. This offset is representative of the distance between the front edge and the middle position of each channel. A reference file including the front edge positions of each of the channels is updated with the determined offset to guide the motion of the scanner 62 to direct the laser beam to the appropriate positions for data collection.

In certain embodiments of the invention, the ruggedized nucleic acid separation/sequencing device 10 further includes a novel system for removing background noise from the signal collected by the fluorescence excitation and detection system 40. Specifically, the fluorescence signal that is collected by the detection system and transmitted to the detectors consists predominantly of two sources, tagged bioanalyte and background. The background component relates to all detectable components except for the tagged bioanalyte and includes fluorescence of the test module 55, any fluorescing elements in the detection path, and background light that is not blocked. This background is of a fixed intensity level and directly adds to the signal from the tagged bioanalyte. In one embodiment of the present invention, baseline subtraction circuitry is implemented to remove the fixed background level from the detector prior to electronic amplification and conversion of the signal from analog to digital form. The removal of background noise (i.e., background offset) allows for a larger dynamic range for signal detection. In prior art systems, detectors convert detected fluorescence (background and signal) into a current, which is then converted into a voltage through electronic amplification. The analog voltage is converted to digital form through an analog to digital converted. In certain embodiments of the present invention, a current source is connected to the detector circuitry, directly after the detector and before electronic amplification, to enable the application of a subtractive current for background removal and leading to a larger dynamic range than prior art devices. In the present invention, the current is controlled electronically and is user selectable.

One of the advantages of the background subtraction system of the present invention over prior art systems is increased signal dynamic range. As a result of the increased signal dynamic range, a larger range of sample concentrations can be detected. For example, a sample collected from a crime scene typically includes a large concentration of a victim's DNA and a small concentration of a perpetrator's DNA. That is, the sample includes a dilute amount of the perpetrator's DNA and a high concentration of the victim's DNA. The background subtraction system of the present invention allows a user to detect a large range of signal/sample concentrations within a single sample without saturating an A/D converter with background noise, while having enough sensitivity to detect the dilute concentration of a second source of DNA (e.g., perpetrator's DNA).

EXAMPLES

The following examples are provided to further illustrate and to facilitate the understanding of the invention. These specific examples are intended to be illustrative of the invention and are not intended to be limiting.

Example 1

The following example illustrates a forensic use of a ruggedized nucleic acid analysis device in accordance with the present invention. In this example, a ruggedized nucleic acid analysis apparatus similar to the one shown in FIGS. 1A, 1B, and 1C was used to analyze a reference sample.

The reference sample consisted of an allelic ladder from a commercially available STR kit (AMPFISTR® SGM PLUS®, from Applied Biosystems, Foster City, Calif.) and size standard (GENESCAN™ 400HD (ROX™) Size Standard, from Applied Biosystems, Foster City, Calif.). The sample was prepared using 2 microliters of allelic ladder, 0.5 microliters of size standard, and 10.5 microliters of deionized water. The sample was denatured prior to analysis by heating the sample to about 90 degrees C. for about 3 minutes followed by rapidly cooling the sample on ice. The sample was then injected into a cleaned microfluidic chip.

Prior to sample injection, the microfluidic chip was cleaned and conditioned to eliminate excess ions in the channels of the chip. Specifically, each channel in the microfluidic chip was filled through a press with 4% LPA sieving material (Dakota Scientific, Sioux Falls, S. Dak.) clean the channels and the anode, cathode, sample arm, and waste arm openings. After cleaning was completed, the anode and cathode openings were filled with 500 microliters of 1×TTE buffer (available from Dakota Scientific, Sioux Falls, S. Dak.), the waste arm opening was filled with 33 microliters of 1×TTE buffer, and the sample arm opening was filled with 13 microliters of deionized water. Each of the channels was conditioned through a preelectrophoresis process in which a 190 V/cm electric field was applied across the cathode and anode for 6 minutes followed by a 875 V/cm electric field was applied across the sample arm and waste arm for 3 minutes.

Following preelectrophoresis, the cathode, anode, sample arm, and waste arm openings were cleaned and then filled. The cathode and anode openings were filed with 500 microliters of 1×TTE buffer, the waste arm opening was filled with 33 microliters of TTE buffer, and the sample arm opening was filled with 13 microliters of the sample as described above.

The sample was loaded into the separation channel by applying a field of 875 V/cm across the sample and waste arms while simultaneously applying a field of 88 V/cm across the anode and cathode for 1.5 minutes. Following loading, the sample was separated and excess sample was pulled back away from the separation channel by applying 190V across the cathode and anode while simultaneously applying 800 V to each of the sample arm and waste arm openings. These conditions were applied to the microfluidic chip for 45 minutes to separate the sample.

Figure 16A:
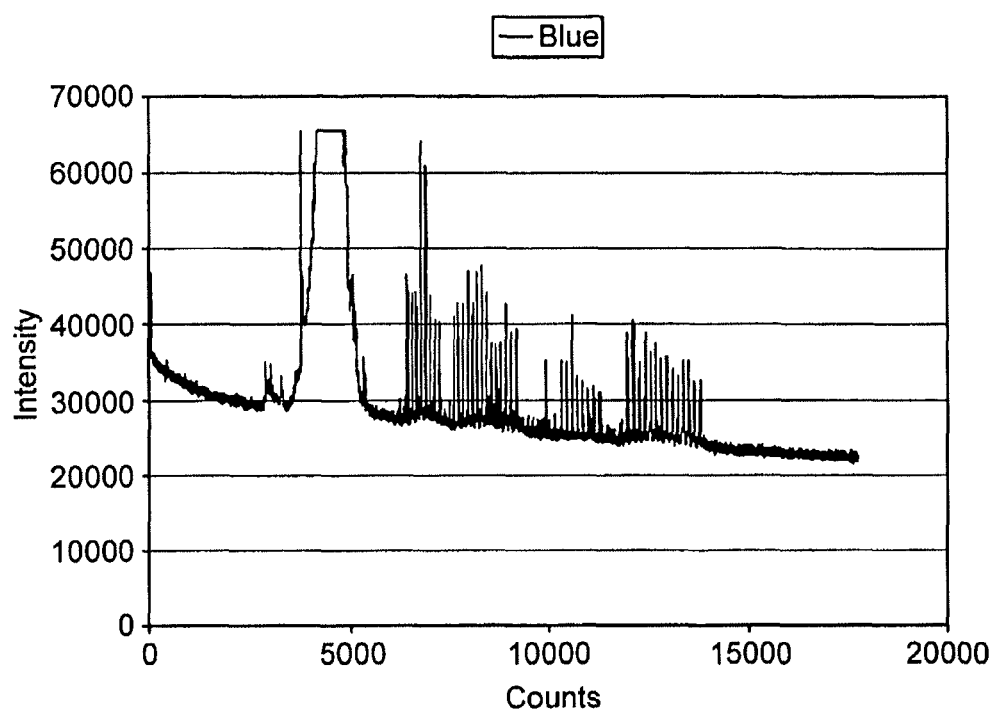
FIGS. 16 A-D are graphs of raw data collected from a sample including a commercially available allelic ladder and a size standard.
Figure 16B:
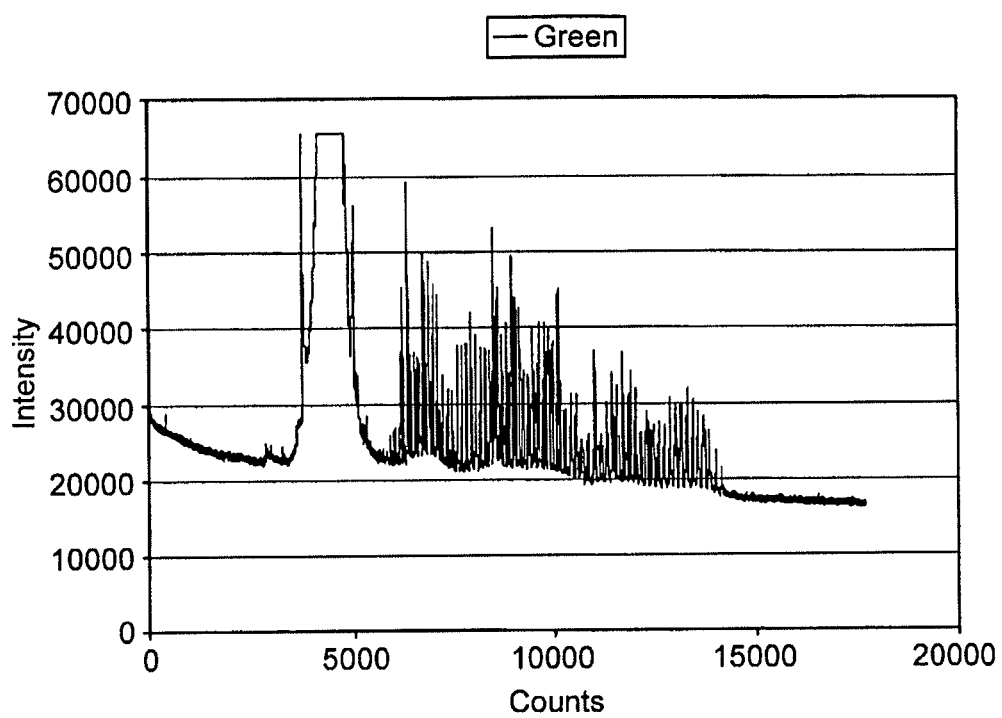
Figure 16C:
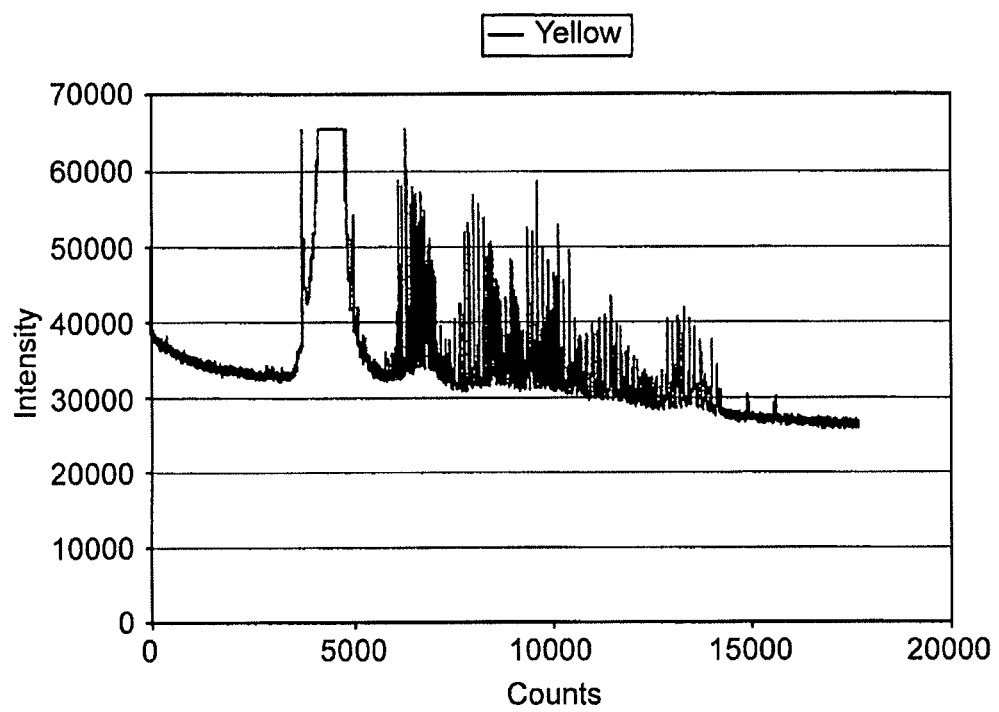
Figure 16D:
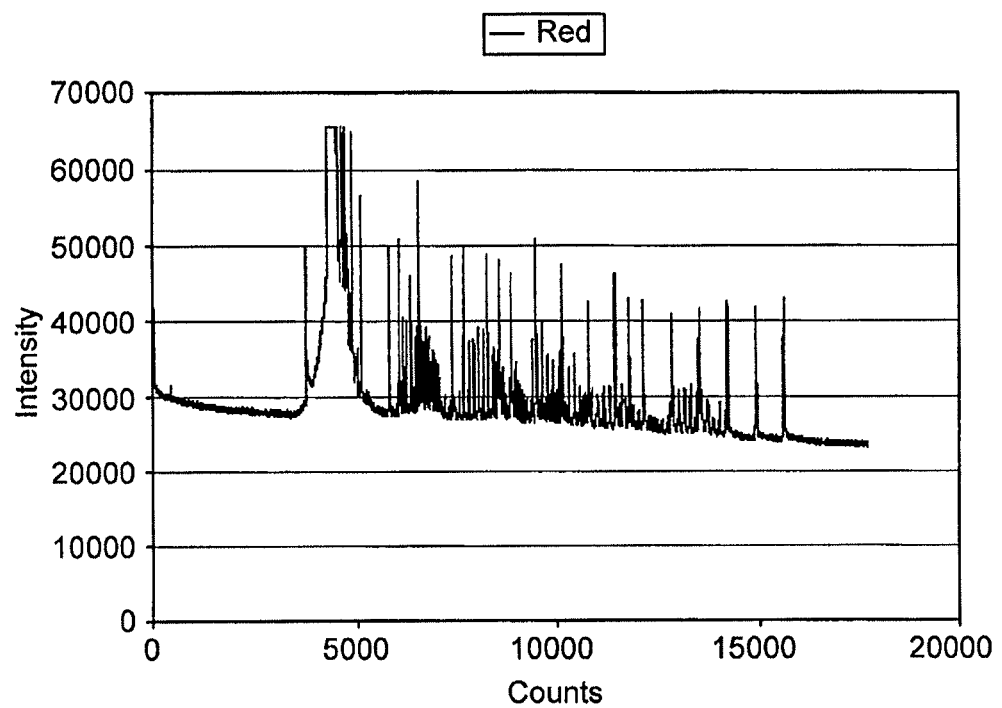

The fluorescence excitation and detection system was then activated to excite fluorescently tagged STR loci within the separated sample. FIGS. 16A, 16B, 16C, and 16D show the raw electrophoregrams of the allelic ladder generated by the data collected by the fluorescence excitation and detection system. Each of the electrophoregrams collected represent one intensity data captured by one of the photomultiplier tubes located within the apparatus. That is FIG. 16A shows the data collected by the photomultiplier tube configured to amplify and detect blue wavelength light, FIG. 16B shows the data collected by the photomultiplier tube configured to amplify and detect green wavelength light, FIG. 16C shows data collected by the photomultiplier tube configured to amplify and detect yellow wavelength light, and FIG. 16D shows data collected by the photomultiplier tube configured to amplify and detect red wavelength light.

Figure 17A:
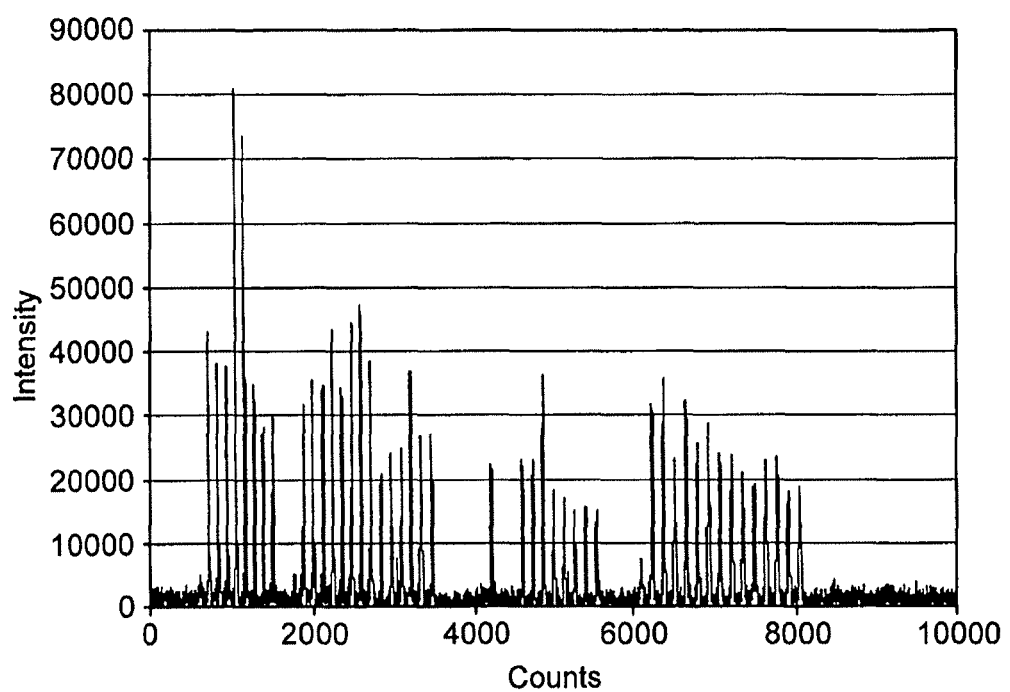
FIGS. 17 A-D are graphs of corrected data of the raw data shown in FIGS. 16 A-D.
Figure 17B:
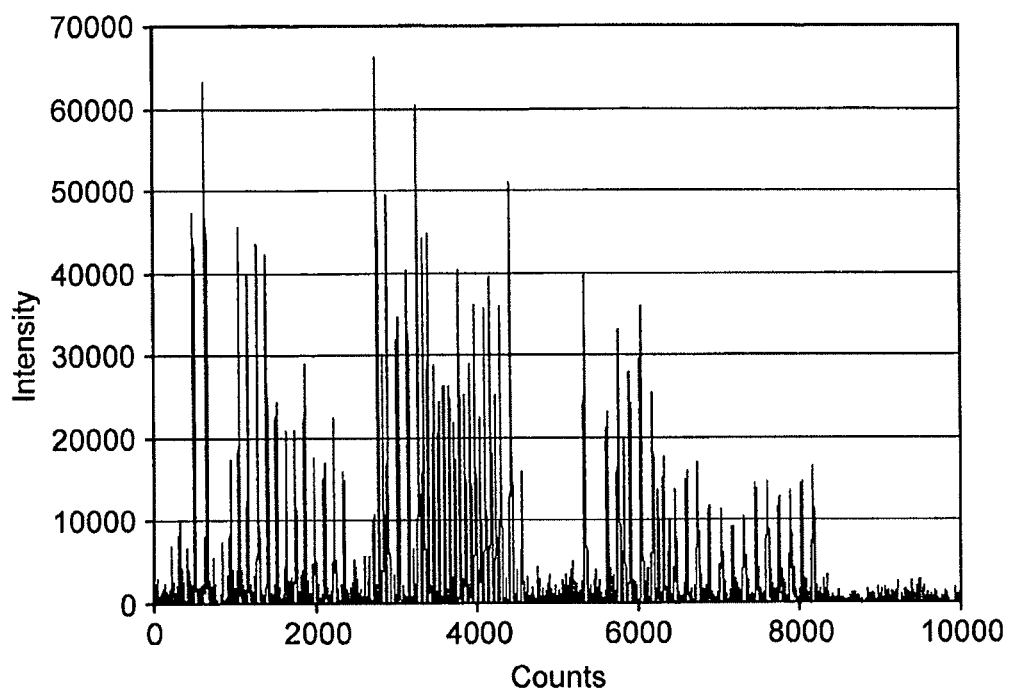
Figure 17C:
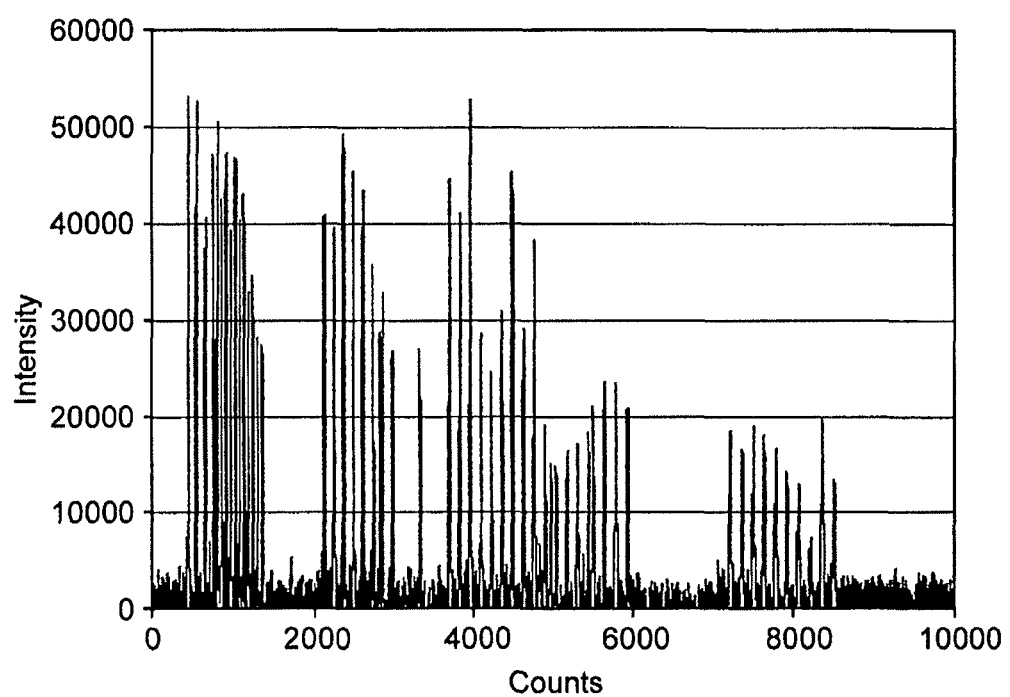
Figure 17D:
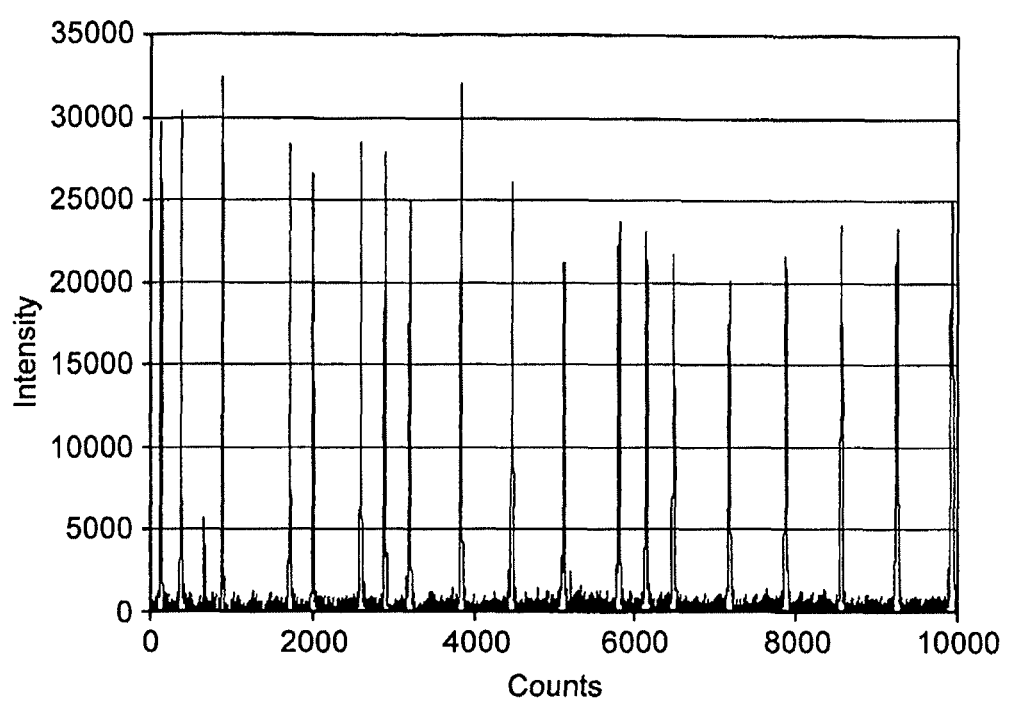

The data from each of the electrophoregrams was corrected using signal processing methods for baseline smoothing, subtraction, and color correction with a 4×4 matrix method as described by L. Li et al. in *Electrophoresis* 1999, volume 20, issue 1, pages 1433-1442, the disclosure of which is hereby incorporated by reference in its entirety. FIGS. 17A, 17B, 17C, and 17D show expanded views of the corrected data. FIG. 17A, which shows the corrected trace of the data for the blue wavelength light, shows the presence of the following loci: D3S1358, VWA, D16S539 and D2S1338 and all of the alleles (i.e., 8, 14, 9, and 14, respectively) associated with each of the loci. In FIG. 17B, the corrected trace of green wavelength light data shows the presence of Amelogenin and loci D8S1179, D21S11, D18S51 and all alleles associate thereto. FIG. 17C shows the corrected trace of yellow wavelength light data. FIG. 17C shows the presence of the following loci: D19S433, TH01, and FGA (both low and high molecular weight sets) together with all alleles associated with each loci. FIG. 17D shows the corrected trace of red wavelength light data. The corrected red wavelength light trace shows size standard peaks at 90, 100, 120, 150, 160, 180, 190, 200, 220, 240, 260, 280, 290, 300, 320, 340, 360, 380, and 400.

Clear identification of all 11 loci associated alleles together with all of the size standards in the sample show that the ruggedized nucleic acid analyzing apparatus has a discrimination ability well suited for forensic analysis. Specifically, the results shown in FIGS. 16A-D and FIGS. 17A-D show that this apparatus has a discrimination power of about 1 to $3.3 \times 10^{12}$.

Example 2

The following example illustrates a DNA sequencing use of a ruggedized nucleic acid analysis device in accordance with the present invention. In this example, a ruggedized nucleic acid analysis device similar to the one shown in FIGS. 1A, 1B, and 1C was used to analyze a sample including a DNA template from an HIV amplicon B.FR.HXB2, with primer GB107. The sample was amplified and labeled with a commercially available cycle sequencing kit (Thermo Sequenase II Dye Terminator Cycle Sequencing Premix Kit) available from Amersham Biosciences, now part of GE Healthcare (Waukesha, Wis.). A cycle sequencing reaction was performed following the manufacturer's recommended procedure. The total sequencing reaction consisted of 750 nanograms of DNA template, 1 microliter of 5 micromolar primer, two microliters of Thermo Sequenase II reagent mix A, 2 microliters of Thermo Sequenase II reagent mix B, and water to bring the total volume to 20 microliters. The reaction was cycled with the following program, with steps 2 through 4 being repeated 30 times: 1) 96 degrees C., 1 minute; 2) 96 degrees C., 30 seconds; 3) 50 degrees C., 15 seconds; 4) 60 degrees C., 1.5 minutes; and 5) 60 degrees C., 5 minutes. The reaction product was stored at 6 degrees C. until ready for use at which time the sample is resuspended in 130 microliters of water and denatured by heating the sample to 70 degrees C. for 3 minutes followed by cooling on ice.

Prior to injecting the sample into the transparent test module the channels of the test module were cleaned and conditioned (i.e., subjected to preelectrophoresis) as described in Example 1. Following preelectrophoresis, the anode, cathode, sample arm, and waste arm openings of the each channel were cleaned and filled. The cathode and anode openings were filled with 500 microliters of 1×TTE buffer available from Dakota Scientific, Sioux Falls, S. Dak. The waste arm opening was filled with 33 microliters of 1×TTE buffer, and the sample arm opening was filed with 13 microliters of the resuspended and denatured sample.

Figure 18A:
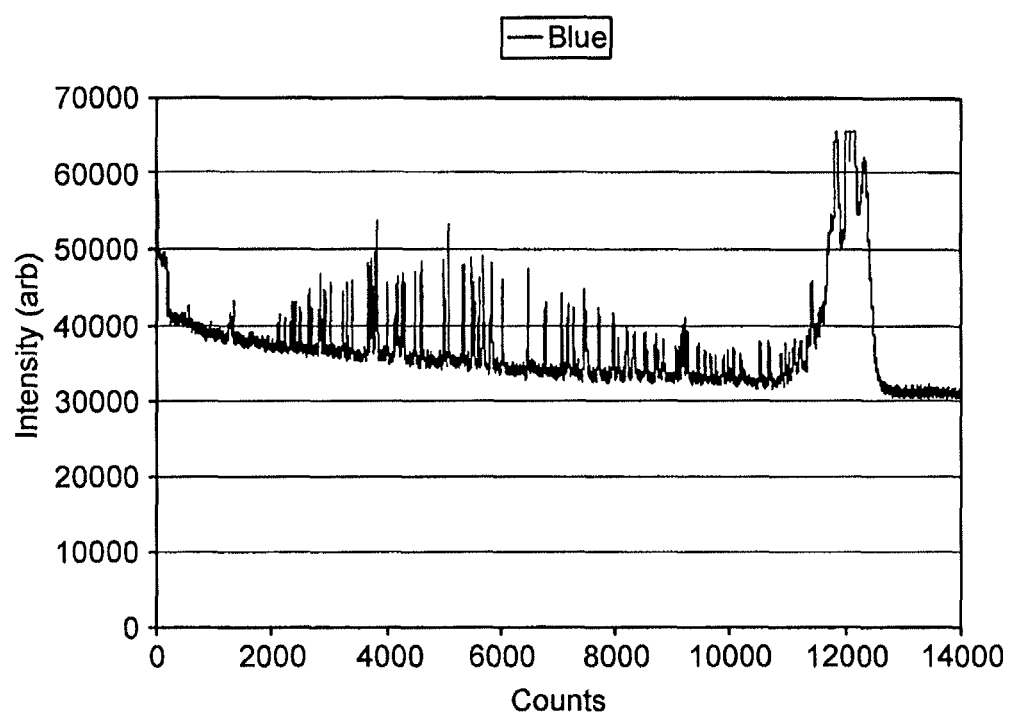
FIGS. 18 A-D are graphs of raw data collected from a sample including a DNA template from an HIV amplicon with primer.
Figure 18B:
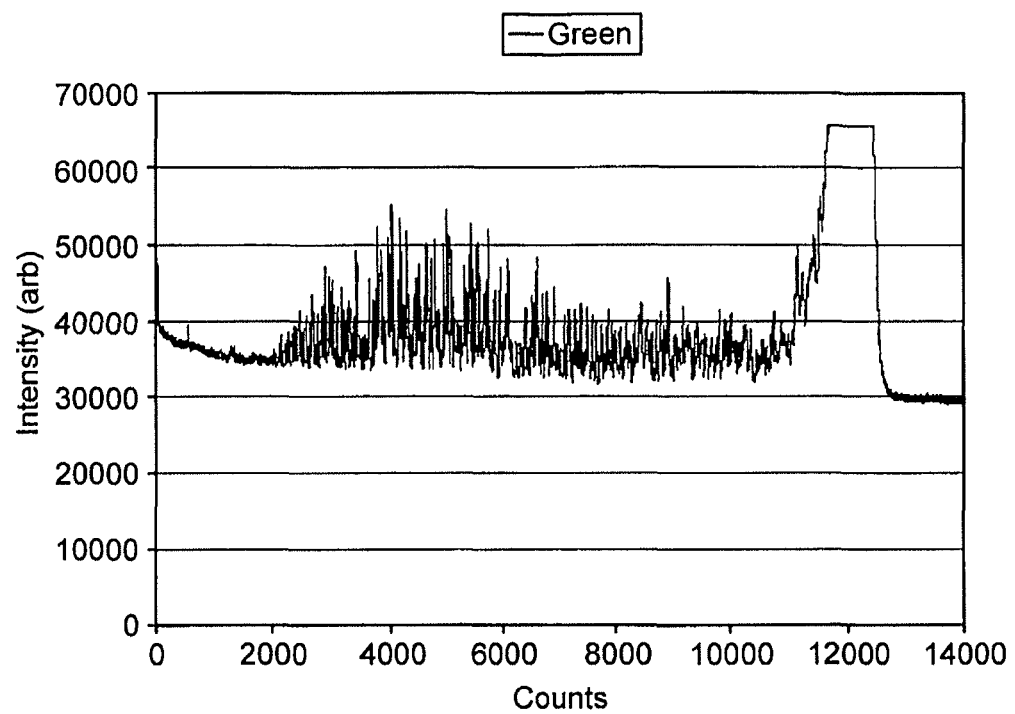
Figure 18C:
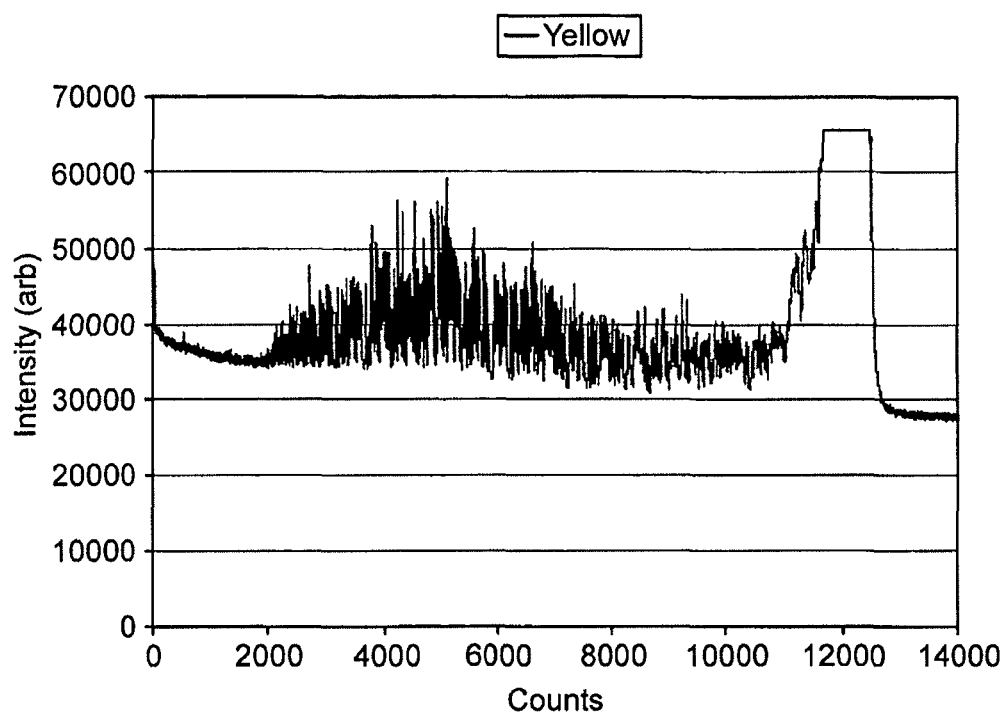
Figure 18D:
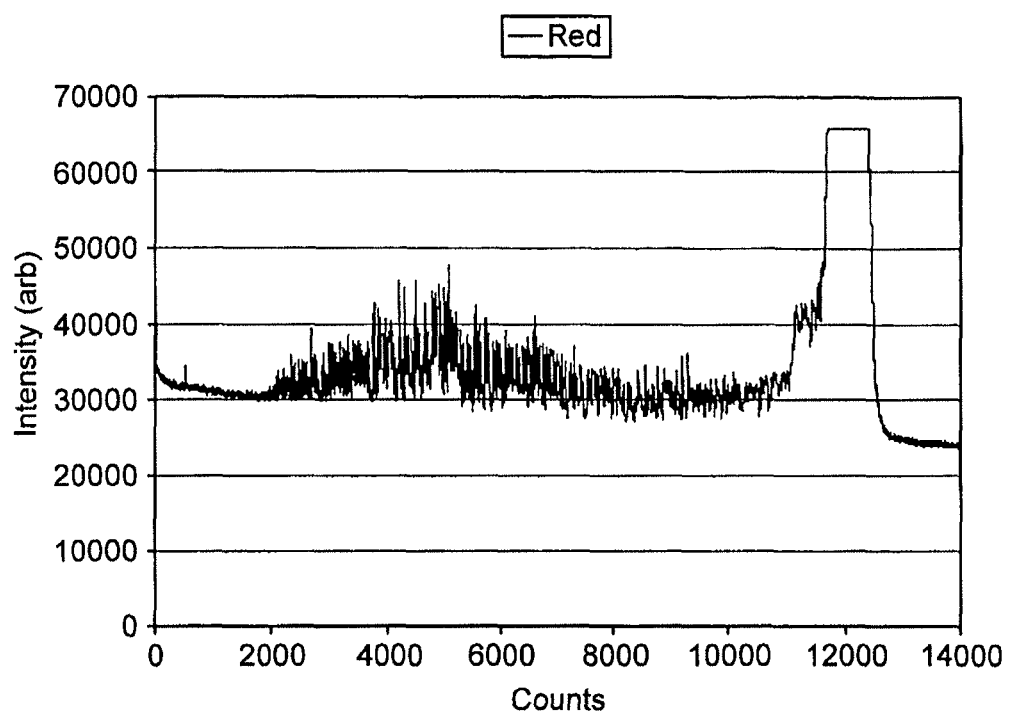

The sample was loaded into the separation channel from the sample arm opening by applying a field of 875 V/cm across the sample arm and waste arm for 60 seconds. The sample was then separated with excess sample being pushed back into the sample and waste arm openings by applying 190 V across the cathode and anode, while simultaneously applying 400 V to each of the sample and waste arm openings. These voltage conditions were applied for 60 minutes to separate the sample The fluorescence excitation and detection system was then activated to excite fluorescently tagged DNA within the separated sample. FIGS. 18A, 18B, 18C, and 18D show the raw electrophoregrams of the DNA sequence generated by the data collected by the fluorescence excitation and detection system. Each of the electrophoregrams collected represent one intensity data captured by one of the photomultiplier tubes located within the apparatus. That is FIG. 18A shows the data collected by the photomultiplier tube configured to amplify and detect blue wavelength light, FIG. 18B shows the data collected by the photomultiplier tube configured to amplify and detect green wavelength light, FIG. 18C shows data collected by the photomultiplier tube configured to amplify and detect yellow wavelength light, and FIG. 18D shows data collected by the photomultiplier tube configured to amplify and detect red wavelength light.

The data from each of the electrophoregrams was corrected using signal processing methods as described by L. Li et al. in *Electrophoresis* 1999, volume 20, issue 1, pages 1433-1442. Further processing of the corrected traces was accomplished by base calling, which associates one of the four nucleotides with each peak in the trace. The traces are smoothed by using a 9-point boxcar average and then the traces are differentiated. Peaks are identified by evaluating the differentiated traces to locate zero crossing with a positive to negative slope change. Peaks identified in the blue wavelength light, green wavelength light, yellow wavelength light and red wavelength light traces are correlated with bases G, A, T, and C, respectively. One skilled in the art of data processing can appreciate the rudimentary nature of this base calling routine, which was used to demonstrate the effectivity of this device. More sophisticated base callers will typically generate longer contiguous reads with the same data as compared to the above described method. A detailed description of base calling can be found at "Base-Calling of Automated Sequencer Traces Using Phred I. Accuracy Assessment" by Ewing et al. in *Genome Research*, 1998, volume 8, pages 175-185 and "Base-Calling of Automated Sequencer Traces Using Phred II. Error Probabilities" by Ewing et al., in *Genome Research*, 1998 volume 8, pages 186-194, the disclosures of which are hereby incorporated by reference in their entirety.

Figure 19A:
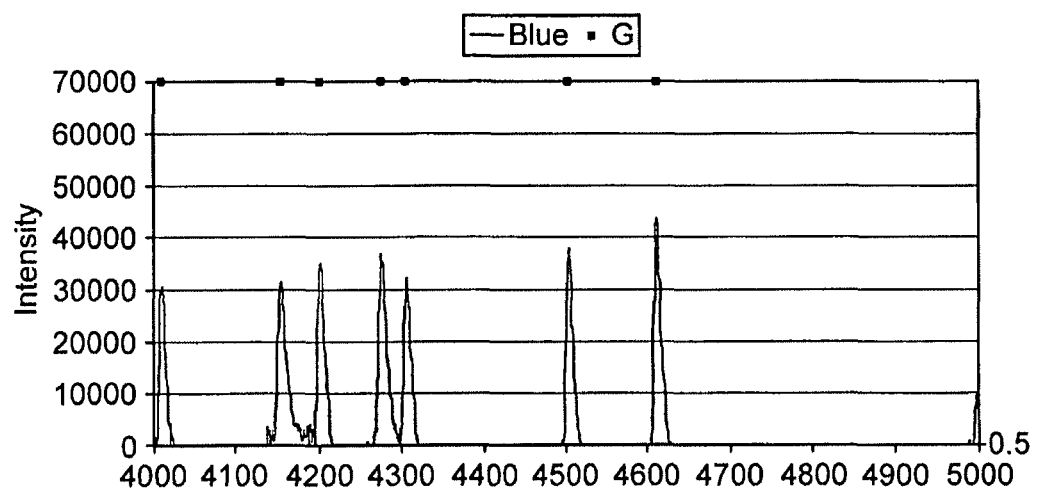
FIGS. 19 A-D are graphs of corrected and base called data the raw data shown in FIGS. 18 A-D.
Figure 19B:
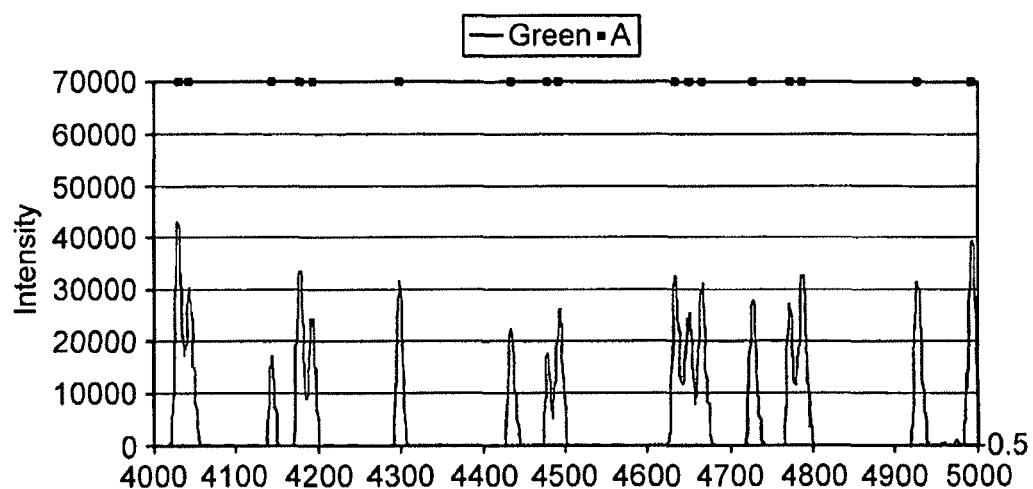
Figure 19C:
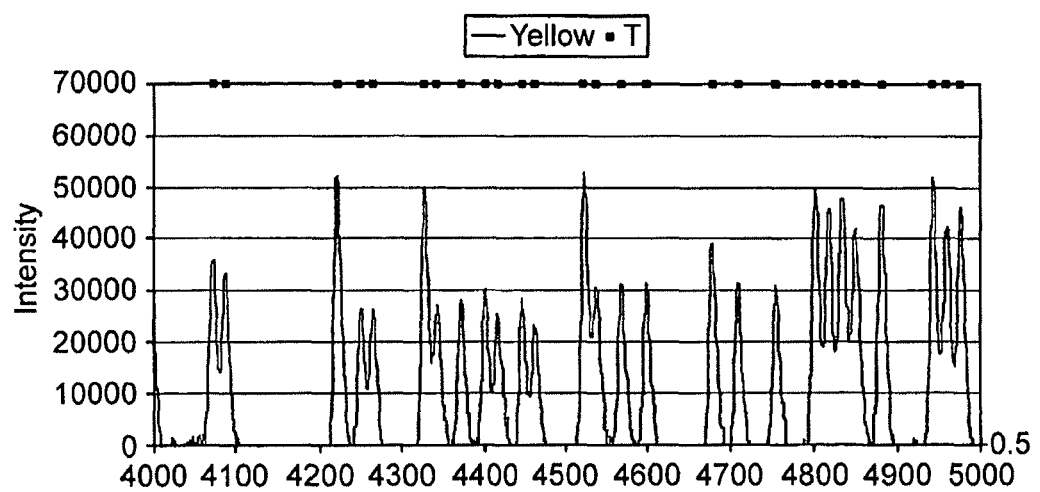
Figures 1, 2, 19D, 20A:
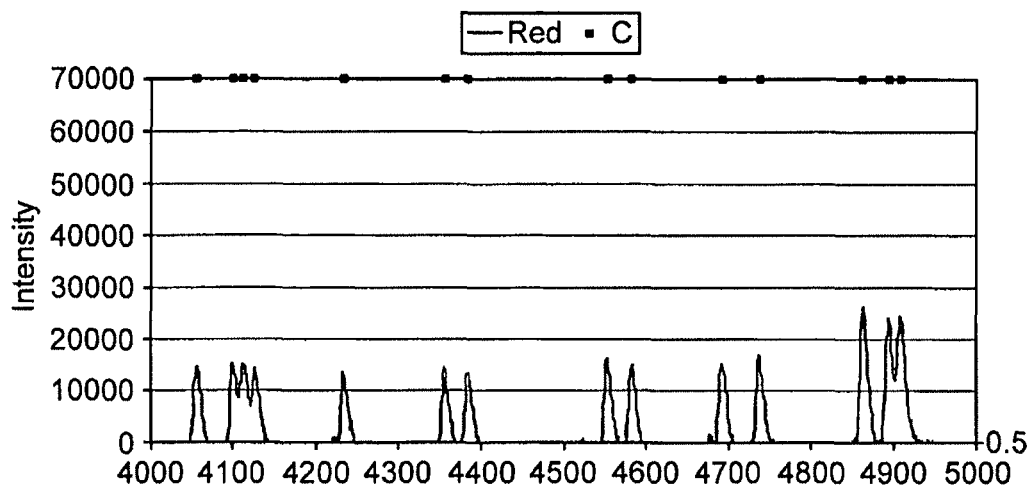

FIGS. 19A, 19B, 19C, and 19D show expanded views of the corrected data. FIG. 19A, which shows the corrected trace of the data for the blue wavelength light, shows the clear identification of the nucleotide guanine. In FIG. 19B, the corrected trace of green wavelength light data shows the clear identification of adenine. FIG. 19C shows the corrected trace of yellow wavelength light data. FIG. 19C shows the clear identification of thymine. FIG. 19D shows the corrected trace of red wavelength light data. The corrected red wavelength light trace shows the identification of cytosine.

Referring to FIGS. 20A, 20B, and 20C, clear identification of the nucleotides associated with the DNA template from the known HIV amplicon B.FR.HXB2 show that the ruggedized nucleic acid analyzing device is well suited for sequencing analysis to be performed at point of care locations. FIG. 20A (i.e., FIG. 20A-1 and FIG. 20A-2) shows a sequence listing of the known amplicon. FIG. 20B shows a sequence listing obtained from analysis of the results generated from the ruggedized nucleic acid analyzing device used in this example. The sequence listing shown in FIG. 20B is unedited and was generated after the data as shown in FIGS. 19A-19D was reverse-complemented using techniques known in the art due to the reverse primer used with this sample. The unedited sequence listing shown in FIG. 20B consists of 378 contiguous bases that exhibit 100% identification with the amplicon of FIG. 20A, from bases 436 to 813. This result is further improved by manually editing the data to remove and replace obvious mistakes incorporated during base calling. FIG. 20C shows the sequence listing obtained after manually editing the data. The edited sequence listing consists of 544 contiguous bases that exhibited 100% identification with the amplicon from bases 297 to 840.

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

For example, while the present invention in certain embodiments has been described as using a transparent test module including one or more microchannels disposed therein, other types of channels can be used. Specifically, the transparent test modules can include channels sized in accordance with standard non-microfluidic capillary electrophoresis procedures. As yet another example, while the present invention has been described as using particular lanefinding scheme to determine the location of the middle of each channel, other lanefinding algorithms can be applied. In certain embodiments of the invention, the lane finding scheme can be modified to detect changes in fluorescence rather than light intensity. In this particular embodiment, photomultiplier tubes are used to capture the reflected signal rather than photodiodes.

SEQUENCE LISTING

<160> NUMBER OF SEQ ID NOS: 3

<210> SEQ ID NO 1
<211> LENGTH: 1692
<212> TYPE: DNA
<213> ORGANISM: Human immunodeficiency virus type 1

<400> SEQUENCE: 1

| | | | | | |
|---|---|---|---|---|---|
| ctagagggaa | ttttcttcag | agcagaccag | agccaacagc | cccaccagaa | gagagcttca | 60 |
| ggtctggggt | agagacaaca | actcccctc | agaagcagga | gccgaaagac | aaggaactgt | 120 |
| atcctttaac | ttccctcaga | tcactctttg | gcaacgaccc | ctcgtcacaa | taaagatagg | 180 |
| ggggcaacta | aaggaagctc | tattagatac | aggagcagat | gatacagtat | tagaagaaat | 240 |
| gagtttgcca | ggaagatgga | aaccaaaaat | gataggggga | attggaggtt | ttatcaaagt | 300 |
| aagacagtat | gatcagatac | tcatagaaat | ctgtggacat | aaagctatag | gtacagtatt | 360 |
| agtaggacct | acacctgtca | acataattgg | aagaaatctg | ttgactcaga | ttggttgcac | 420 |
| tttaaatttt | cccattagcc | ctattgagac | tgtaccagta | aaattaaagc | caggaatgga | 480 |
| tggcccaaaa | gttaaacaat | ggccattgac | agaagaaaaa | ataaaagcat | tagtagaaat | 540 |
| ttgtacagaa | atggaaaagg | aagggaaaat | ttcaaaaatt | gggcctgaga | atccatacaa | 600 |
| tactccagta | tttgccataa | agaaaaaaga | cagtactaaa | tggagaaaat | tagtagattt | 660 |
| cagagaactt | aataagagaa | ctcaagactt | ctgggaagtt | caattaggaa | taccacatcc | 720 |
| cgcagggtta | aaaaagaaaa | aatcagtaac | agtactggat | gtgggtgatg | catattttc | 780 |
| agttcccttá | gatgaagact | tcaggaagta | tactgcattt | accataccta | gtataaacaa | 840 |
| tgagacacca | gggattagat | atcagtacaa | tgtgcttcca | cagggatgga | aaggatcacc | 900 |
| agcaatattc | caaagtagca | tgacaaaaat | cttagagcct | tttaaaaaac | aaaatccaga | 960 |
| catagttatc | tatcaataca | tggatgattt | gtatgtagga | tctgacttag | aaatagggca | 1020 |
| gcatagaaca | aaaatagagg | agctgagaca | acatctgttg | aggtggggat | ttaccacacc | 1080 |
| agacaaaaaa | catcagaaag | aacctccatt | cctttggatg | ggttatgaac | tccatcctga | 1140 |
| taaatggaca | gtacagccta | tagtgctgcc | agaaaaagac | agctggactg | tcaatgacat | 1200 |
| acagaagtta | gtggggaaat | tgaattgggc | aagtcagatt | tacccaggga | ttaaagtaag | 1260 |
| gcaattatgt | aaactcctta | gaggaaccaa | agcgctaaca | gaagtaatac | cactaacaga | 1320 |
| agaagcagag | ctagaactgg | cagaaaacag | agagattcta | aaagaaccag | tacatggagt | 1380 |
| gtattatgac | ccatcaaaag | acttaatagc | agaaatacag | aagcaggggc | aaggccaatg | 1440 |
| gacatatcaa | atttatcaag | agccatttaa | aaatctgaaa | acaggaaaat | atgcaagaag | 1500 |
| gaggggtgcc | cacactaatg | atgtaaaaca | attaacagag | gcagtgcaaa | aaataaccac | 1560 |
| agaaagcata | gtaatatggg | aaagactcc | taaatttaaa | ctacccatac | aaaaggaaac | 1620 |
| atgggaaaca | tggtggacag | agtattggca | agccacctgg | attcctgagt | gggagtttgt | 1680 |
| taataccct | cg | | | | | 1692 |

<210> SEQ ID NO 2
<211> LENGTH: 378
<212> TYPE: DNA
<213> ORGANISM: Human immunodeficiency virus type 1

<400> SEQUENCE: 2

| | | | | | |
|---|---|---|---|---|---|
| tagccctatt | gagactgtac | cagtaaaatt | aaagccagga | atggatggcc | caaaagttaa | 60 |
| acaatggcca | ttgacagaag | aaaaaataaa | agcattagta | gaaatttgta | cagaaatgga | 120 |

```
aaaggaaggg aaaatttcaa aaattgggcc tgagaatcca tacaatactc cagtatttgc      180
cataaagaaa aaagacagta ctaaatggag aaaattagta gatttcagag aacttaataa      240
gagaactcaa gacttctggg aagttcaatt aggaatacca catcccgcag ggttaaaaaa      300
gaaaaaatca gtaacagtac tagatgtggg tgatgcatat ttttcagttc ccttagatga      360
agacttcagg aagtatac                                                    378

<210> SEQ ID NO 3
<211> LENGTH: 544
<212> TYPE: DNA
<213> ORGANISM: Human immunodeficiency virus type 1

<400> SEQUENCE: 3
aagtaagaca gtatgatcag atactcatag aaatctgtgg acataaagct ataggtacag       60
tattagtagg acctacacct gtcaacataa ttggaagaaa tctgttgact cagattggtt      120
gcactttaaa ttttcccatt agccctattg agactgtacc agtaaaatta aagccaggaa      180
tggatggccc aaaagttaaa caatggccat tgacagaaga aaaaataaaa gcattagtag      240
aaatttgtac agaaatggaa aaggaaggaa aaatttcaaa aattgggcct gagaatccat      300
acaatactcc agtatttgcc ataaagaaaa aagacagtac taaatggaga aaattagtag      360
atttcagaga acttaataag agaactcaag acttctggga agttcaatta ggaataccac      420
atcccgcagg gttaaaaaag aaaaaatcag taacagtact ggatgtgggt gatgcatatt      480
tttcagttcc cttagatgaa gacttcagga agtatactgc atttaccata cctagtataa      540
acaa                                                                   544
```

What is claimed is:

1. An electrophoresis system for finding the position of at least one separation channel, the system comprising:
   (A) a removable test module comprising a transparent material that allows at least a part of a fluorescence excitation energy beam to interact with said at least one capillary disposed within said removable test module, said at least one capillary, further comprising a separation channel and a detection zone; and
   (B) an electrophoresis instrument capable of receiving said removable test module said electrophoresis instrument comprising;
      (1) a fluorescence excitation and detection system further comprising: a fluorescence excitation beam source, producing, in use, said fluorescence excitation energy beam, that is capable of interacting with said at least one capillary by deflection and travelling along the length of said removable test module, and of intersecting said detection zone of said at least one capillary when inserted into said electrophoresis instrument, and
      (2) at least one light detector positioned on a first side of said removable test module when inserted into said electrophoresis instrument, and further positioned to detect a signal from light that has travelled through said at least one capillary, and which has been deflected thereby, as said signal is exiting said removable test module, said fluorescence excitation beam source configured such that said fluorescence excitation energy beam is capable of intersecting the detection zone of said at least one capillary when inserted into said electrophoresis instrument; and
      (3) a processor configured to direct said fluorescence excitation energy beam source to transmit said fluorescent excitation energy beam towards said detection zone and to receive data collected by said at least one light detector,
   wherein in use, at least a part of said fluorescence excitation energy beam is transmitted through the removable test module, and deflected light travels within the test module and along its length and is detected by said at least one light detector to generate an intensity pattern that is used by the processor to determine the position of the middle of each of said at least one channel.

2. The system as claimed in claim 1, wherein the fluorescence excitation beam is a laser beam.

3. The system as claimed in claim 1, wherein said at least one light detector is a photodiode.

4. The system as claimed in claim 1 comprising a first detector and a second detector placed on either side of said removable test module.

5. The system as claimed in claim 4 wherein said first and second detectors are photodiodes.

6. The system of claim 1 or 2 or 3 or 5 where said at least one capillary is microfluidic.

7. The system of claim 4 wherein said at least one capillary is microfluidic.

* * * * *